(12) United States Patent
Luyken et al.

(10) Patent No.: US 9,012,638 B2
(45) Date of Patent: *Apr. 21, 2015

(54) PROCESS FOR PREPARING EDDN AND/OR EDMN BY CONVERSION OF FACH AND EDA

(75) Inventors: Hermann Luyken, Ludwigshafen (DE); Sebastian Ahrens, Wiesloch (DE); Gordon Brasche, Frankfurt (DE); Jens Baldamus, Ludwigshafen (DE); Robert Baumann, Mannheim (DE); Randolf Hugo, Dirmstein (DE); Stephanie Jaegli, Mannheim (DE); Johann-Peter Melder, Böhl-Iggelheim (DE); Jörg Pastre, Bensheim (DE); Boris Buschhaus, Mannheim (DE)

(73) Assignee: BASF SE, Ludwigshafen (DE)

( * ) Notice: Subject to any disclaimer, the term of this patent is extended or adjusted under 35 U.S.C. 154(b) by 162 days.

This patent is subject to a terminal disclaimer.

(21) Appl. No.: 13/599,325

(22) Filed: Aug. 30, 2012

(65) Prior Publication Data

US 2013/0090452 A1  Apr. 11, 2013

Related U.S. Application Data

(60) Provisional application No. 61/529,280, filed on Aug. 31, 2011.

(51) Int. Cl.
| | | |
|---|---|---|
| *C07D 241/04* | (2006.01) | |
| *C07C 253/30* | (2006.01) | |
| *C07C 209/48* | (2006.01) | |
| *C07D 295/00* | (2006.01) | |

(52) U.S. Cl.
CPC ............. *C07C 253/30* (2013.01); *C07C 209/48* (2013.01)

(58) Field of Classification Search
USPC ............................ 544/382; 564/490; 528/422
See application file for complete search history.

(56) References Cited

U.S. PATENT DOCUMENTS

| | | |
|---|---|---|
| 3,896,051 A | 7/1975 | Mabuchi et al. |
| 3,947,522 A | 3/1976 | Shelley, Jr. et al. |
| 4,895,994 A | 1/1990 | Cheng et al. |
| 5,530,127 A | 6/1996 | Reif et al. |
| 5,874,607 A | 2/1999 | Schnurr et al. |
| 6,518,449 B1 | 2/2003 | Boschat et al. |
| 2001/0025119 A1 | 9/2001 | Voit et al. |
| 2002/0058842 A1 | 5/2002 | Ansmann et al. |

(Continued)

FOREIGN PATENT DOCUMENTS

| | | |
|---|---|---|
| DE | 19614283 A1 | 10/1997 |
| EP | 696572 A1 | 2/1996 |

(Continued)

OTHER PUBLICATIONS

European Search Report for EP11179583 (European equivalent) mailed Jan. 27, 2012.

(Continued)

*Primary Examiner* — Duc Truong
(74) *Attorney, Agent, or Firm* — Drinker Biddle & Reath LLP

(57) ABSTRACT

A process for reacting formaldehyde cyanohydrin (FACH) with ethylenediamine (EDA) in a reactor with limited backmixing at a temperature in the range from 20 to 120° C., wherein the residence time in the reactor is 300 seconds or less.

17 Claims, 3 Drawing Sheets

(56) References Cited

U.S. PATENT DOCUMENTS

| | | |
|---|---|---|
| 2007/0043217 A1 | 2/2007 | Siegert et al. |
| 2010/0029991 A1 | 2/2010 | Dahmen et al. |
| 2010/0056828 A1 | 3/2010 | Oftring et al. |
| 2010/0121064 A1 | 5/2010 | Dahmen et al. |
| 2010/0121109 A1 | 5/2010 | Dahmen et al. |
| 2011/0137029 A1 | 6/2011 | Kubanek et al. |
| 2011/0137030 A1 | 6/2011 | Kubanek et al. |
| 2011/0178329 A1 | 7/2011 | Bock et al. |
| 2011/0182798 A1 | 7/2011 | Bohling et al. |
| 2011/0207634 A1 | 8/2011 | Baumann et al. |
| 2011/0207651 A1 | 8/2011 | Baumann et al. |
| 2011/0218270 A1 | 9/2011 | Suter et al. |
| 2011/0251433 A1 | 10/2011 | Wigbers et al. |
| 2011/0251434 A1 | 10/2011 | Muller et al. |
| 2011/0257431 A1 | 10/2011 | Baumann et al. |
| 2011/0288326 A1 | 11/2011 | Luyken et al. |
| 2011/0288337 A1 | 11/2011 | Chedid et al. |
| 2011/0294977 A1 | 12/2011 | Schaub et al. |
| 2012/0004464 A1 | 1/2012 | Huyghe et al. |
| 2012/0022310 A1 | 1/2012 | Schneider et al. |
| 2012/0029225 A1 | 2/2012 | Magerlein et al. |
| 2012/0052316 A1 | 3/2012 | Evstatieva et al. |
| 2012/0071692 A1 | 3/2012 | Ahrens et al. |
| 2012/0095221 A1 | 4/2012 | Wigbers et al. |
| 2012/0108816 A1 | 5/2012 | Wigbers et al. |
| 2012/0157679 A1 | 6/2012 | Wigbers et al. |
| 2012/0157715 A1 | 6/2012 | Pape et al. |
| 2012/0165585 A1 | 6/2012 | Schneider et al. |
| 2012/0203022 A1 | 8/2012 | Franzke et al. |
| 2012/0203045 A1 | 8/2012 | Coelho Tsou et al. |
| 2012/0209024 A1 | 8/2012 | Bock et al. |
| 2012/0232292 A1 | 9/2012 | Schaub et al. |
| 2012/0232293 A1 | 9/2012 | Schaub et al. |
| 2012/0232294 A1 | 9/2012 | Schaub et al. |
| 2012/0232309 A1 | 9/2012 | Schaub et al. |
| 2012/0245377 A1 | 9/2012 | Bock et al. |
| 2012/0245389 A1 | 9/2012 | Wigbers et al. |
| 2012/0245390 A1 | 9/2012 | Wigbers et al. |
| 2012/0253072 A1 | 10/2012 | Franzke et al. |
| 2012/0253077 A1 | 10/2012 | Jodecke et al. |
| 2012/0264973 A1 | 10/2012 | Baumann et al. |
| 2012/0271068 A1 | 10/2012 | Magerlein et al. |

FOREIGN PATENT DOCUMENTS

| | | |
|---|---|---|
| EP | 892777 A1 | 1/1999 |
| EP | 963975 A1 | 12/1999 |
| EP | 1 209 146 A1 | 5/2002 |
| EP | 1742045 A1 | 1/2007 |
| WO | WO-99/33561 A1 | 7/1999 |
| WO | WO-99/44984 A1 | 9/1999 |
| WO | WO-2005037769 A1 | 4/2005 |
| WO | WO-2008/104582 A2 | 9/2008 |
| WO | WO-2008104553 A1 | 9/2008 |
| WO | WO-2008104578 A1 | 9/2008 |
| WO | WO-2008104579 A1 | 9/2008 |
| WO | WO-2008104583 A1 | 9/2008 |

OTHER PUBLICATIONS

U.S. Appl. No. 13/600,877, filed Aug. 31, 2012.
U.S. Appl. No. 13/598,691, filed Aug. 30, 2012.
U.S. Appl. No. 13/598,715, filed Aug. 30, 2012.
U.S. Appl. No. 13/598,712, filed Aug. 30, 2012.
U.S. Appl. No. 13/599,270, filed Aug. 30, 2012.
U.S. Appl. No. 13/598,698, filed Aug. 30, 2012.
U.S. Appl. No. 13/598,750, filed Aug. 30, 2012.
U.S. Appl. No. 13/598,685, filed Aug. 30, 2012.
U.S. Appl. No. 13/598,769, filed Aug. 30, 2012.
U.S. Appl. No. 13/600,662, filed Aug. 31, 2012.
U.S. Appl. No. 13/600,848, filed Aug. 31, 2012.
International Search Report (In German) for PCT/EP2012/066619, mailing date Oct. 15, 2012.
International Search Report (In German) for PCT/EP2012/066830, mailing date Oct. 18, 2012.
International Search Report (In German) for PCT/EP2012/066640, mailing date Oct. 19, 2012.
International Search Report (In German for PCT/EP2012/066833, mailing date Oct. 24, 2012.
International Search Report (In German) for PCT/EP2012/066808, mailing date Oct. 25, 2012.
International Search Report (In German) for PCT/EP2012/066170, mailing date Nov. 15, 2012.
International Search Report (In German) for PCT/EP2012/066646, mailing date Nov. 15, 2012.
International Search Report (In German) for PCT/EP2012/066586, mailing date Dec. 7, 2012.
International Search Report (In German) for PCT/EP2012/066584, mailing date Feb. 12, 2013.

PROCESS FOR PREPARING EDDN AND/OR EDMN BY CONVERSION OF FACH AND EDA

CROSS REFERENCE TO RELATED APPLICATION

The present application incorporates the provisional U.S. application 61/529,303 filed on Aug. 31, 2011 by reference.

BACKGROUND OF THE INVENTION

The present invention relates to a process for preparing EDDN and/or EDMN by reaction of FACH with EDA, the conversion being performed in a reactor with short residence time. The present invention also relates to the preparation of TETA and/or DETA by conversion of the EDDN or EDMN thus prepared with hydrogen in the presence of a catalyst. The present invention further provides for the preparation of epoxy resins, amides or polyamides from the DETA or TETA obtained in accordance with the invention.

WO 2008/104579 and the prior art cited in WO 2008/104579 specify various preparation methods for EDDN and EDMN.

In WO 2008/104579, EDDN is prepared by reacting EDA with formaldehyde (FA) and hydrogen cyanide (HCN) with a molar ratio of EDA to FA to HCN of 1:1.5:1.5 to 1:2:2 [mol:mol:mol]. The preparation can be effected by a) reacting EDA with FACH with a molar ratio of EDA to FACH of 1:1.5 to 1:2, or b) preparing EDDN by reaction of an ethylenediamine-formaldehyde adduct (EDFA) with hydrogen cyanide with a molar ratio of EDFA to HCN of 1:1.5 to 1:2, or c) reacting EDA with a mixture of formaldehyde and hydrogen cyanide with a molar ratio of EDA to FA to HCN of 1:1.5:1.5 to 1:2:2, or d) reacting EDA simultaneously with formaldehyde and HCN with a molar ratio of EDA to FA to HCN of 1:1.5:1.5 to 1:2:2.

It is disclosed that these reactions are preferably performed at a temperature of 10 to 90° C. and at standard pressure to slightly elevated super-atmospheric pressure. Preferred reactors are described as being a tubular reactor or a stirred tank cascade. The reaction output formed is preferably worked up by distillation, first removing low boilers such as hydrogen cyanide in a first stage and removing water in a second distillation step. The remaining aminonitrile mixture may have a residual water content of preferably at least 10% by weight. WO 2008/104579 discloses, in the examples, residence times for the reaction of EDA with FACH in the range from 30 minutes to 2 hours.

SUMMARY OF THE INVENTION

In the context of the present invention it has been found that especially aqueous solutions of EDDN and EDMN are thermally unstable. EDDN and EDMN can form decomposition products which can reduce the yield of EDDN or EDMN and can lead in further reactions, for example the subsequent hydrogenation to give TETA and/or DETA, to a worsened processing quality, more particularly to an increase in discoloration.

It was an object of the present invention to provide a process for preparing EDDN and/or EDMN that allows the preparation of EDDN and/or EDMN with high yields, conversions and selectivities on an industrial scale. The fraction of unwanted byproducts, especially of the decomposition products of EDDN and/or EDMN, ought to be reduced as compared with the prior art.

Furthermore, the process ought to provide EDDN and/or EDMN which in downstream reactions, such as the hydrogenation to give TETA or DETA, respectively, leads to product discoloration to a lesser extent, and allows a longer service life for the hydrogenation catalyst.

The object was achieved by a process for reacting formaldehyde cyanohydrin (FACH) with ethylenediamine (EDA) in a reactor with limited backmixing at a temperature in the range from 20 to 120° C., wherein the residence time in the reactor is 300 seconds or less.

A BRIEF DESCRIPTION OF THE FIGURES

A DETAILED DESCRIPTION OF THE INVENTION

Figure 1:
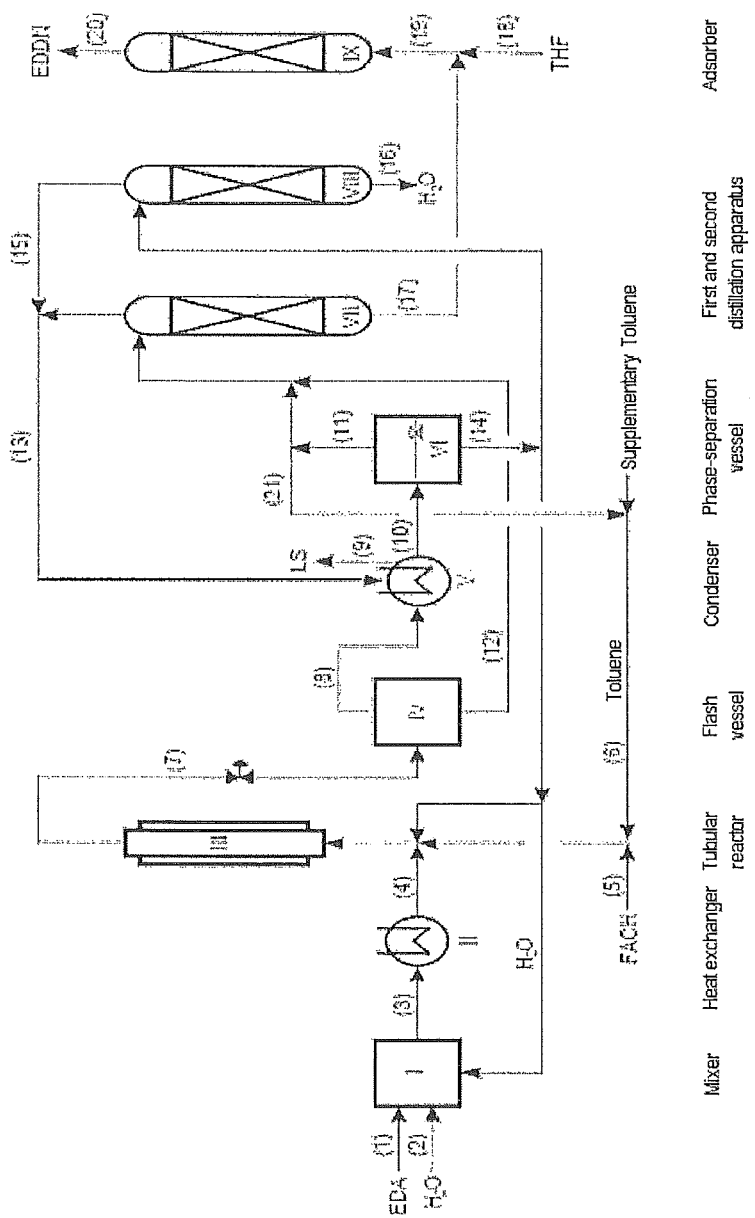
FIG. 1 shows the preparation of EDDN or EDMN from EDA (1) and FACH (5).

EDDN and/or EDMN is prepared by conversion of FACH using EDA.

EDA

EDA can be prepared by the EDC (ethylene dichloride) process by reaction of ethylene dichloride (EDC) with ammonia in the aqueous phase. Details of the process are given, for example, in Ullmann (article "Amines, aliphatic" in Ullmann's Encyclopedia of Industrial Chemistry, Karsten Eller, Erhard Henkes, Roland Rossbacher and Hartmut Höke, Published Online: Jun. 15, 2000, DOI: 10.1002/14356007.a02_001, page 33).

A further means of preparing EDA consists in the catalytic reaction of monoethanolamine (MEOA) with ammonia (article "Amines, aliphatic" in Ullmann's Encyclopedia of Industrial Chemistry, Karsten Eller, Erhard Henkes, Roland Rossbacher and Hartmut Höke, Published Online: Jun. 15, 2000, DOI: 10.1002/14356007.a02_001, page 33 or Hans-Jürgen Arpe, Industrielle Organische Chemie [Industrial Organic Chemistry], 6th edition (2007), Wiley VCH, 2007).

EDA can also be obtained by hydrogenation of aminoacetonitrile (AAN), AAN being preparable by reaction of hydrogen cyanide, formaldehyde (FA) and ammonia.

The hydrogenation of AAN to EDA is described, for example, in WO 2008/104583.

EDA is preferably used in the form of its free base, but it is optionally also possible to use salts such as the dihydrochloride of EDA as the reactant.

The purity of the EDA used in the process is preferably 95% by weight or more, more preferably 98% by weight or more, even more preferably 99% by weight or more and especially preferably 99.5% by weight or more.

FACH Preparation

The preparation of FACH is described, for example, in Ullmann (article "Formaldehyde" in Ullmann's Encyclopedia of Industrial Chemistry, Günther Reuss, Walter Disteldorf, Armin Otto Gamer and Albrecht Hilt, Published Online: Jun. 15, 2000, DOI: 10.1002/14356007.a11_619, p. 28). It can be prepared, for example, by reacting formaldehyde with an aqueous hydrogen cyanide.

Formaldehyde and hydrogen cyanide are likewise—as described above—chemicals widely available commercially.

Preference is given to using formaldehyde, as described above, at a 30 to 50% aqueous solution.

Hydrogen cyanide can, as described above, be used in gaseous form or as an aqueous solution.

A preferred variant for preparation of FACH is described in WO 2008/104579. According to this, the preparation of FACH can be effected by reaction of aqueous formaldehyde with hydrogen cyanide. Formaldehyde is preferably in the form of a 30 to 50% aqueous solution; hydrogen cyanide is preferably used in 90 to 100% purity. This reaction is effected preferably at a pH of 5.5, which is preferably established with sodium hydroxide solution or ammonia. The reaction can be effected at temperatures of 20 to 70° C., for example in a loop reactor and/or tubular reactor. Instead of purified hydrogen cyanide (HCN), it is also possible to chemisorb crude HCN gas into FACH in an aqueous formaldehyde solution under the conditions specified above. The crude HCN gas is preferably prepared by pyrolysis of formamide and comprises, as well as water, small proportions of ammonia in particular. The resulting aqueous FACH solution can optionally be concentrated by gentle vacuum concentration, for example with a falling-film or thin-film evaporator. Preference is given to concentrating to a 50-80% by weight aqueous FACH solution. Before the concentration, it is advantageous to stabilize the FACH solution by lowering the pH to ≤4, preferably to ≤3, for example by adding acid, for example by adding phosphoric acid or preferably sulfuric acid.

Preferably, a 50 to 80% by weight aqueous solution of FACH is used in the process according to option a).

FA

A reactant used for the preparation of FACH is formaldehyde.

Formaldehyde is a chemical widely available commercially.

Preference is given to using formaldehyde as a 30 to 50% aqueous solution.

HCN

In addition, hydrogen cyanide is used to prepare FACH.

Hydrogen cyanide is likewise a chemical widely available commercially.

Hydrogen cyanide can be prepared on the industrial scale essentially by three different processes. In a first process, hydrogen cyanide can be obtained by ammoxidation of methane with oxygen and ammonia (Andrussow process). In a second process, hydrogen cyanide can be obtained from methane and ammonia by ammodehydrogenation in the absence of oxygen.

Finally, hydrogen cyanide can be prepared on the industrial scale by dehydration of formamide. In general, an acidic stabilizer is added to the hydrogen cyanide prepared by these processes, for example $SO_2$, sulfuric acid, phosphoric acid or an organic acid such as acetic acid, in order to prevent the autocatalytic polymerization of hydrogen cyanide, which can lead to blockages in pipelines.

Hydrogen cyanide can be used in liquid or gaseous form, in pure form or as an aqueous solution.

Hydrogen cyanide is preferably used as a 50 to 95% by weight, more preferably as a 75 to 90% by weight, aqueous solution.

Hydrogen cyanide is preferably used in a purity of 90% by weight or more.

Preference is given to using stabilizer-free HCN.

If a stabilized HCN is used, it is preferable that the stabilizer is an organic acid, especially acetic acid.

In a preferred embodiment, the EDDN preparation is performed with substantial freedom from cyano salts such as KCN.

Water

The conversion of EDA and FACH preferably takes place in the presence of water.

The reaction of EDA and FACH generally gives rise to 1 mol of water per mole of formaldehyde used.

However, water can also be supplied additionally, for example by using the reactants in the form of aqueous solutions thereof. More particularly as described above, it is generally possible to use FA and/or HCN as an aqueous solution to prepare FACH.

The amount of water is generally in the range from 1 to 50 mol per mole, preferably in the range from 2 to 40 mol and more preferably in the range from 3 to 30 mol per mole of EDA used.

If EDA and FACH are converted in an adiabatic reactor, i.e. a reactor which is essentially not cooled and the reaction temperature is increased by the heat of reaction released, it is preferable that EDA is mixed with water before being introduced into the adiabatic reactor and before being mixed with the other starting materials, such as FACH, since the mixing of EDA and water generally increases the temperature of the aqueous EDA stream as a result of the exothermicity of the hydrates which form. By leading off the heat of EDA hydration before the entry of the EDA into the reactor, the temperature rise in the adiabatic reactor can be reduced. Suitable apparatuses for the mixing of EDA and water are static mixers, empty pipes with turbulent flow, pumps or heat exchangers.

To lead off the heat of hydration, water is mixed with EDA preferably in a molar ratio of water to EDA of 1:1 to 6:1.

Organic Solvent

The conversion of EDA and FACH preferably takes place in the presence of an organic solvent. The organic solvents used are preferably those selected from the group consisting of aliphatic, cycloaliphatic, araliphatic, aromatic hydrocarbons, alcohols and ethers.

It is especially preferable that the organic solvent is stable under the conditions of a subsequent hydrogenation of EDDN and/or EDMN.

It is also preferable that the organic solvent is condensable within the range from 20 to 50° C. at a pressure in the range from 50 to 500 mbar, in order to be able to use standard cooling water in the subsequent workup of EDDN or EDMN for condensing.

It is also preferable that the organic solvent boils at a sufficiently low temperature to be able to establish a bottom temperature less than 100° C. in the subsequent removal of water during the workup of the reaction output.

Preferred organic solvents are, for example, cyclohexane, methylcyclohexane, toluene, N-methylmorpholine, o-xylene, m-xylene or p-xylene, anisole, n-pentane, n-hexane, n-heptane, n-octane, n-nonane, diisobutyl ether, light gasoline, gasoline, benzene, diglyme, tetrahydrofuran, 2- and 3-methyltetrahydrofuran (MeTHF) and cyclohexanol, or mixtures of these compounds. Particularly preferred solvents are cyclohexane, methylcyclohexane, toluene, N-methylmorpholine, o-xylene, m-xylene or p-xylene, anisole, n-pentane, n-hexane, n-heptane, n-octane, n-nonane, diisobutyl ether, light gasoline, gasoline (benzene), diglyme and MeTHF, or mixtures of these compounds.

The amount of organic solvent is generally 0.1 to 50 kg per kg, preferably 1 to 30 kg and more preferably 3 to 25 kg per kg of EDA used.

In a particularly preferred process variant, in the conversion of EDA and FACH, an organic solvent having a boiling point between water and EDDN or EDMN is used, especially under the conditions of the distillative depletion of water described below. As described below, organic solvents which boil within this range enable particularly efficient removal of water from the reaction output which is obtained in the conversion of FACH and EDA. Particularly preferred solvents having a boiling point between water and EDDN or EDMN are toluene, N-methylmorpholine, o-xylene, m-xylene or p-xylene, anisole, n-octane, n-nonane, diisobutyl ether or diglyme, or mixtures thereof.

Some of the aforementioned organic solvents can form a low-boiling azeotrope with water. A low-boiling azeotrope corresponds, in the p, x diagram, to the substance mixture at the maximum vapor pressure. The boiling point of this mixture has a minimum in the T, x diagram and is below that of the pure substances involved.

Particularly preferred organic solvents which have a boiling point between water and EDDN or EDMN and which form a low-boiling azeotrope with water are toluene, N-methylmorpholine, o-xylene, m-xylene or p-xylene, anisole, n-octane, n-nonane, diisobutyl ether and diglyme, or mixtures thereof.

If the organic solvent having a boiling point between water and EDDN and/or EDMN forms a low-boiling azeotrope with water, it is also preferred that the organic solvent has a miscibility gap or sparing solubility in water, more particularly under the conditions of the workup steps described hereinafter. This facilitates the later separation of water and organic solvents. The solubility of such an organic solvent is preferably 1% by weight or less, more preferably 0.5% by weight or less and especially preferably 0.1% by weight or less. In particular, toluene is preferred as such an organic solvent.

In a further preferred embodiment, in the conversion of FACH and EDA, an organic solvent which has a boiling point below the boiling point of water and which forms a low-boiling azeotrope with water, especially under the conditions of the distillative removal of water described below, is used.

Particularly preferred solvents which have a boiling point below the boiling point of water and which form a low-boiling azeotrope with water are n-pentane, n-hexane, n-heptane, tetrahydrofuran, cyclohexane, methylcyclohexane, light gasoline, gasoline (benzene) or mixtures thereof. Such a solvent under standard conditions should preferably have a boiling point of at least 50° C. and more preferably of at least 60° C. in order thus to attain sufficiently high condensation temperatures that the use of brine in the condenser can be avoided.

It is additionally preferred that the solvent used which has a boiling point below the boiling point of water and which forms a low-boiling azeotrope with water has a low solubility in water or a miscibility gap with water under the conditions which exist in the conversion of FACH and EDA or the subsequent workup. This facilitates the later separation of water and organic solvents. The solubility of such an organic solvent in water is preferably 1% by weight or less, more preferably 0.5% by weight or less and especially preferably 0.1% by weight or less.

In a very particularly preferred embodiment, the conversion of EDA and FACH to EDDN and/or EDMN is performed in the presence of toluene as a solvent, and the subsequent hydrogenation of EDDN and/or EDMN to TETA and/or DETA is performed in the presence of THF. As described below, it is thus possible to establish a particularly efficient integrated solvent system which allows the recycling of the organic solvents into the process. In addition, it has been recognized that the presence of THF during the subsequent hydrogenation, especially when the hydrogenation is performed in suspension mode, can reduce the agglomeration tendency of the suspension catalysts used.

Accordingly, a particularly preferred embodiment of the present invention relates to the preparation of TETA and/or DETA by hydrogenating EDDN and/or EDMN with hydrogen in the presence of a catalyst, wherein EDDN and/or EDMN is prepared from FACH and EDA in the presence of toluene as a solvent and the hydrogenation is performed in suspension mode in the presence of THF.

More particularly, it is preferable that THF is fed in after the EDDN and/or EDMN preparation, and that the EDDN and/or EDMN preparation is followed by a treatment of EDDN or EDMN with an adsorbent, preferably a solid acidic adsorbent, in the presence of THF.

Conversion of FACH and EDA (General)

Processes for converting EDA and FACH in the presence of water are described, for example in WO 2008/104579, the contents of which are explicitly incorporated by reference.

According to the invention, FACH and EDA are converted in a reactor with a limited backmixing at a temperature in the range from 20 to 120° C., with a short residence time.

Accordingly, this present invention relates to the reaction of formaldehyde cyanohydrin (FACH) with ethylenediamine (EDA) in a reactor with limited backmixing at a temperature in the range from 20 to 120° C., wherein the residence time in the reactor is 300 seconds or less.

According to the invention, the conversion of FACH and EDA is performed in a reactor with limited backmixing.

Examples of a reactor with limited backmixing are a tubular reactor and a stirred tank cascade. Particular preference is given to performing the reaction of FACH and EDA in a tubular reactor ("plug flow reactor").

The ratio of height to diameter of the tubular reactor is preferably 1:1 to 500:1, more preferably 2:1 to 100:1 and especially preferably 5:1 to 50:1.

The tubular reactor may comprise internals which counteract backmixing. The internals may, for example, be balls, baffles, sieve trays or static mixers.

The tubular reactor used is most preferably an empty tube.

The position of the reactor is unimportant. It may be upright or horizontal, or may be configured as a spiral or tie bolt.

According to the invention, the residence time in the reaction of FACH with EDA in the reactor within the temperature range claimed is 300 seconds or less, preferably 200 seconds or less, more preferably 100 seconds or less and especially preferably 60 seconds or less.

The residence time is preferably in the range from 1 to 300 seconds, more preferably 5 to 200 seconds, even more preferably 10 to 100 seconds and especially preferably 15 to 60 seconds.

In the context of the present invention, the residence time $\tau$ is defined as the quotient of reactor volume $V_R$ and exit volume flow rate $\dot{V}(\tau=V_R/\dot{V})$, where the reactor volume comprises the volume from the reactor inlet as far as the reactor outlet.

In the context of the present invention, the reactor inlet corresponds to the mixing point at which FACH and EDA are contacted.

In the context of the present invention, the reactor outlet corresponds to the point at which the temperature of the reaction mixture is lowered by cooling.

The reaction mixture can be cooled at the reactor outlet, as described below, preferably by
  removing heat by means of a heat exchanger,
  feeding in an organic solvent, or
  flash evaporation.

In the first case, the reactor outlet corresponds to the point at which the reaction mixture enters the heat exchanger for cooling.

In the second case, the reactor outlet corresponds to the last mixing point at the outlet of the reactor, at which further organic solvent is supplied for cooling.

In the third case, the reactor outlet corresponds to the decompression valve by which the reaction mixture, as described below, is partially evaporated.

Thus, the reactor volume may also comprise the parts of the pipelines or feed lines to the reactor which are between the reactor inlet (mixing site, at which EDA and FACH are contacted) and the reactor outlet (e.g. decompression valve, inlet to the heat exchanger or the last mixing point at the outlet of the reactor, at which organic solvent is supplied for cooling).

In a very particularly preferred embodiment, the FACH-containing stream and the aqueous EDA stream are mixed at the inlet of the reactor. The mixing can be effected by means of static mixers, suitable internals such as random packings, especially Raschig rings, or by the generation of turbulent flow at and downstream of the mixing site. For example, turbulent flow can be effected by injecting one of the reactants into the other reactant.

More preferably, EDA is reacted with FACH, in the very particularly preferred embodiment, under adiabatic conditions, which means that the reaction temperature is increased by the heat of reaction released.

According to the invention, it is required that the reaction temperature does not exceed 120° C., since increased decomposition of the EDDN and EDMN target products has been observed above this temperature in the context of this invention.

In order to limit the temperature rise in the reactor to temperatures in the range from 20 to 120° C., it is possible to perform several technical measures, preferably:

the reactants and any organic solvent and any water can be cooled before they are introduced into the reactor to temperatures in the range from 10 to 50° C., preferably 20 to 40° C. and more preferably 25 to 35° C.;

the reactor or part of the reactor can be provided with cooling apparatus; or an organic solvent can be fed into the reaction mixture.

It is also possible to perform one or more of the abovementioned measures in combination.

The reactants, and any organic solvent and water, can be introduced into the reactor at a temperature in the range from 10 to 50° C., preferably 15 to 40° C. and more preferably 20 to 35° C. If the temperature of the reactants should be above these preferred ranges, the reactants can be cooled down with suitable cooling apparatus, for example heat exchangers, especially plate heat exchangers, shell and tube heat exchangers or jacketed heat exchangers.

The reactor or part of the reactor may alternatively or additionally be provided with cooling apparatus. For example, the reactor may have jacket cooling. It is also possible that elements which can remove heat are present in the reactor, for example internal heat exchangers. In addition, it is also conceivable that a proportion of the reactor contents is conducted through a loop with a heat exchanger therein. However, additional cooling apparatus generally means higher apparatus and construction complexity, but these are also suitable for keeping the temperature in the reactor within the inventive range.

In a further embodiment, the reaction mixture can be cooled by feeding in further organic solvents before or during the reaction. The total amount of organic solvent should, however, preferably not be above 50 kg per kg of EDA, preferably 30 and more preferably 25 kg per kg of EDA. The organic solvent is preferably introduced into the reactor for cooling at a temperature in the range from 10 to 50° C., preferably 15 to 40° C. and more preferably 20 to 35° C.

By taking the measures mentioned above, especially the addition of organic solvent, the exit temperatures can be kept within the range from 50 to 120° C., preferably within the range from 60 to 110° C. and more preferably within the range from 70 to 100° C. It is especially preferable when the cooling is effected both by addition of organic solvent and by cooling of the tubular reactor by means of a cooling jacket.

As described, the reaction mixture is additionally cooled at the outlet of the reactor. The cooling of the reaction mixture can be effected, for example, by cooling by means of suitable cooling apparatus, feeding in further organic solvent, or by flash evaporation. The cooling of the reaction mixture at the outlet of the reactor is described in detail below.

According to the selection of the appropriate process parameters (for example reactant, temperature, solvent or pressure), the process can be controlled such that the proportion of EDMN in the reaction product varies, and EDMN is not obtained as a by-product but as a second main reaction product.

Preferably, the ratio of EDDN to EDMN in the conversion of FACH and EDA is influenced by the molar ratio of the reactants—as described below.

In general, the molar ratio of EDA to FACH in the reaction of EDA with FACH is in the range from 1:1 to 1:2 [mol/mol].

Preferably, the molar ratio of EDA to FACH is about 1:1.8 to 1:2 [mol/mol], especially approx. 1:2 [mol/mol].

If the EDDN content in the reaction mixture is to be increased, the molar ratio of EDA to FACH is preferably 1:1.5 to 1:2, more preferably 1:1.8 to 1:2. A high EDDN content in the reaction mixture is advantageous when EDDN is to be hydrogenated to TETA in a subsequent reaction. If the EDMN content in the reaction mixture is to be increased, the molar ratio of EDA to FACH is preferably 1:1 to 1:1.5, more preferably 1:1 to 1:1.3. A high EDMN content in the reaction mixture is advantageous when EDMN is to be hydrogenated to DETA in a subsequent reaction.

Especially preferably, the conversion is performed in the presence of one of the aforementioned organic solvents, especially the organic solvents specified as preferred and particularly preferred. The amount of solvent used is—as described above—generally 0.1 to 50 kg per kg, preferably 1 to 30 kg and more preferably 3 to 25 kg per kg of EDA used.

A particularly advantageous organic solvent has been found to be toluene, which enables a technically simple and efficient process in a subsequent removal of water.

FACH is preferably mixed with an organic solvent, one of the aforementioned organic solvents, especially toluene, to give an FACH-containing stream, for which either fresh organic solvent or organic solvent which is recovered from the subsequent workup can be used.

EDA is, as described above, likewise preferably mixed with water before being introduced into the reactor to give an aqueous EDA stream when the subsequent reaction with FACH is effected in an adiabatic reactor. For instance, the heat of hydration which arises when water and EDA are mixed can already be removed upstream of the reactor.

In a particularly preferred embodiment, an organic solvent is fed into the reaction mixture before it is introduced into the reactor, in order to achieve a limitation of the adiabatic temperature increase when the reaction is performed in an adiabatic reactor, i.e. in a reactor which is essentially not cooled and in which the reaction temperature is increased by the heat of reaction released. The organic solvents used can contribute to a limitation of the temperature rise by absorbing heat of reaction in accordance with their heat capacity and contributing to a smaller temperature rise. In general, the higher the amount of solvent fed in, the greater the extent to which the temperature rise can be limited.

The organic solvent is preferably cooled or added at ambient temperature, in order that it can absorb heat. The organic solvent is preferably introduced into the reactor at a temperature in the range from 10 to 50° C., preferably 15 to 45° C. and more preferably 20 to 40° C.

The use of organic solvents can—as described below—also accelerate cooling of the reaction mixture after it leaves the reactor, for example by decompressing the solvent-containing reaction mixture such that at least a portion of the organic solvent evaporates. The additional evaporation of the organic solvent can additionally remove heat from the reaction mixture.

Preferably, the reaction mixture is cooled at or downstream of the exit from the reactor, especially when the reaction is performed in an adiabatic reactor. The cooling of the reaction mixture can be performed as described above and in detail below.

Reaction Output

The reaction output obtained is generally a mixture of EDDN and EDMN.

The ratio of EDDN to EDMN can be influenced, as described above, generally by the ratio of the reactants used.

The weight ratio of EDDN to EDMN is generally 30:70 to 95:5, preferably 50:50 to 95:5, more preferably 75:25 to 90:10.

The reaction output may comprise organic solvent.

The reaction output preferably comprises one of the organic solvents specified above or specified as preferred and particularly preferred. More particularly, the reaction output comprises toluene.

The reaction output more preferably comprises 5 to 30% by weight and even more preferably 10 to 20% by weight and especially preferably 12 to 18% by weight of toluene, based on the reaction output. Especially preferably, the reaction output comprises, aside from toluene, essentially no further organic solvents.

The reaction output generally comprises water, which forms as water of reaction in the conversion of FACH and EDA, or which has been fed in together with the reactants or separately.

The reaction output which is obtained in the preparation of EDDN or EDMN can be worked up further by methods known to those skilled in the art. This relates, for example, to the removal of the reaction product from unconverted reactant and any solvent present.

Cooling of the output from the conversion of EDA and FACH

In a very particularly preferred embodiment, the reaction mixture from the conversion of EDA and FACH is cooled after leaving the reactor and before being worked up.

Accordingly, the very particularly preferred embodiment relates to the preparation of EDDN and/or EDMN by conversion of FACH and EDA, the reaction being effected in the presence of water, wherein the reaction mixture from the conversion of EDA and FACH is cooled after leaving the reactor.

Cooling of the reaction mixture from the conversion of FACH and EDA is preferred especially when the last stage of the reaction has been performed in an adiabatic reactor, especially a tubular reactor.

It is additionally preferred that the temperature after the cooling is within the range from 20 to 70° C., more preferably in the range from 20 to 60° C. and especially preferably in the range from 30 to 50° C. By means of rapid cooling to the temperature range specified, it is possible that unwanted by-products, for example decomposition products of the nitriles, are reduced further. The reaction mixture can be cooled by means of suitable cooling apparatus, such as heat exchangers, especially plate heat exchangers, shell and tube heat exchangers or jacketed heat exchangers.

It is also possible that further organic solvent is fed into the cooling. As mentioned above, the total amount of organic solvent should, however, preferably not be above 50 kg per kg of EDA, preferably 30 and more preferably 25 kg per kg of EDA. Preferably, the organic solvent is introduced into the reactor for cooling at a temperature in the range from 10 to 50° C., preferably 15 to 40° C. and more preferably 20 to 35° C.

The cooling is most preferably effected by flash evaporation.

For this purpose, the reaction mixture from the EDDN or EDMN preparation is decompressed through a valve at the outlet of the last reactor in which the EDDN or EDMN preparation is effected into a vessel with reduced pressure. The reduced pressure is preferably adjusted such that some of the water used and of the component having lower boiling points than EDDN or EDMN in the reaction output is converted to the gas phase and the reactants, such as EDDN or EDMN, and some of the water, and any organic solvent, remain in the liquid phase.

The flash evaporation removes a portion of the water from the reaction mixture in a gentle manner. As a result of the heat of evaporation removed, the liquid EDDN- or EDMN-containing phase is cooled. The two effects, cooling and reduction of the water concentration, generally stabilize the EDDN or EDMN present. Side reactions are generally reduced as a result.

Preferably 10 to 80% by weight, more preferably 20 to 70% by weight and most preferably 30 to 60% by weight of the water present in the reaction mixture is evaporated in the flash evaporation and converted to the gas phase.

The reduced pressure is preferably 1000 mbar or less, more preferably 300 mbar or less and most preferably 200 mbar or less.

In a preferred embodiment, the reduced pressure is 10 to 1000 mbar, preferably 50 to 300 mbar and more preferably 100 to 200 mbar.

The fraction of the components present in gaseous form after the flash evaporation is preferably partially condensed in a condenser, the condensation preferably being operated such that water and any solvent used are essentially completely condensed. Lower-boiling components, for example ammonia, HCN, methanol or $CO_2$, are preferably not condensed and can be removed in gaseous form or sent to incineration.

The workup of the condensed phase can be guided by whether the reaction of EDA with FACH has been performed in the presence of an organic solvent, and by which organic solvent has been used.

If no organic solvent is used, in the preparation of EDDN or EDMN, the aqueous condensate can be supplied to the column K2 described hereinafter, in which low boilers are separated from water. It is also possible to supply the water to a disposal, for example by wastewater treatment.

If an organic solvent which is miscible with water or has no miscibility gap with water is used, the condensed mixture of organic solvent and water is generally separated by distillation into an aqueous stream and a solvent-containing stream, and the solvent-containing stream can preferably be recycled into the process or introduced into a column K1 described hereinafter. The aqueous stream can generally be introduced into a water treatment.

If, in a preferred embodiment, the organic solvent used is a solvent which has a miscibility gap with water or which is essentially insoluble in water, the condensed mixture is preferably supplied to a phase separator, such that the condensed phase can be separated into a phase comprising the organic solvent and an aqueous phase.

The use of an organic solvent which has a miscibility gap with water or is essentially insoluble in water allows the separation of organic solvent and water generally without additional distillation. In addition, the water removed, after the phase separation, can then generally be introduced directly into a water treatment plant or recycled into the process, for example for mixing of EDA with water.

In this respect, organic solvents in which the amount of solvent dissolved in the aqueous phase is very low (preferably less than 5000 ppm) are particularly preferred. Examples thereof are toluene, cyclohexane, methylcyclohexane, octane, heptane and xylenes.

The aqueous phase obtained after the phase separation can also be introduced into a distillation apparatus K2, in which water as the bottom product is removed from lower-boiling organic components. The water thus removed can be recycled, for example, as a solvent into the process (for example for preparation of an aqueous EDA solution) or sent to a water treatment plant or a biological wastewater treatment. The organic low boilers removed via the top in the distillation in column K2 (for example organic solvents having a lower boiling point than water or solvents which form a low-boiling azeotrope with water, HCN or toluene) are preferably recycled into the process. For example, the organic low boilers can be supplied to the condenser connected downstream of the flash evaporation.

The organic phase obtained after the phase separation is preferably passed into the column K1 described hereinafter or recycled into the process as organic solvent.

The EDDN- or EDMN-comprising reaction output, which is in the liquid phase after the flash evaporation into the vessel with reduced pressure, is preferably, as described below, supplied to a distillation column K1 in which water is depleted from EDDN or EDMN.

If an organic solvent which has a miscibility gap with water or a low solubility in water under the conditions of the EDDN or EDMN preparation has been used in the EDDN or EDMN preparation, typically two liquid phases form in the vessel in which the output from the EDDN or EDMN preparation has been decompressed, namely an aqueous EDDN or EDMN phase and a phase comprising the organic solvent.

Preferably, the two phases, as described hereinafter, are supplied separately or together to a column K1. It is additionally preferred that, when the column K1 comprises random packings, both liquid phases should be conducted separately from one another on separate liquid dividers.

After the cooling, the reaction output obtained in the preparation of EDDN or EDMN can be worked up further by methods known to those skilled in the art. This relates, for example, to the removal of the reaction product from unconverted reactant and any solvent present.

Workup of the Reaction Output from the EDDN or EDMN Preparation

As mentioned above, the reaction output obtained in the preparation of EDDN or EDMN can be worked up further by methods known to those skilled in the art. This relates, for example, to the removal of the reaction product from unconverted reactant and any solvent present.

Preferably, the reaction output from the EDDN or EDMN preparation is worked up by performing first i) a low boiler removal and then ii) a water depletion.

Low Boiler Depletion

The low boilers are preferably depleted by stripping. For example, the reaction output from the EDDN or EDMN preparation can be stripped with nitrogen in order to remove traces of hydrogen cyanide which may occur, for example, as a decomposition product of FACH.

However, low boilers can also be removed by distillation. If low boilers are removed by distillation, it is preferable that the residence time in the distillation is kept brief, for example by performing the distillation in a falling-film evaporator or wiped-film evaporator.

The low boiler removal is preferably effected, as described above, by flash evaporation. Flash evaporation has the advantage that the low boiler removal and cooling of the reaction output can be effected in one process step.

Water Depletion

The water depletion after the depletion of low boilers is preferably effected in a distillation column K1.

The column is generally operated in such a way that an aqueous stream is drawn off at the top of the column, while an EDDN- or EDMM-containing stream is drawn off at the bottom of the column.

The output from the EDDN or EDMN preparation is preferably supplied to a distillation column K1 together with the distilling agent (see definition hereinafter) in the upper region, preferably at the top.

If the output from the EDDN or EDMN preparation has been cooled by flash evaporation, and if an organic solvent which has a miscibility gap with water or a low solubility in water under the conditions of the EDDN or EDMN preparation has been used in the EDDN or EDMN preparation, as described above, two liquid phases form in the vessel in which the output from the EDDN or EDMN preparation has been decompressed. In this case, it is preferable that the aqueous EDDN or EDMN phase which forms and the organic solvent as a distilling agent are supplied separately from one another to column K1. It is additionally preferable that, when column K1 comprises random packings, the two liquid phases should be conducted onto separate liquid distributors. It is preferable to recycle the organic solvent as a distilling agent into the stripping section of the column, preferably into the lower region of the column and more preferably into the bottom of the column. This has the advantage that HCN present in the recycled organic solvent can react with EDMN to give EDDN. This can reduce the amount of HCN discharged.

Preferably, the distillation column K1 has internals for increasing the separating performance. The distillative internals may be present, for example, in the form of a structured packing, for example as a sheet metal packing such as Mellapak 250 Y or Montz Pak, B1-250 type. It is also possible for a packing with lower or increased specific surface area to be present, or it is possible to use a fabric packing or a packing with another geometry such as Mellapak 252 Y. An advantage in the case of use of these distillative internals is the low pressure drop and the low specific liquid holdup compared, for example, to valve trays. The internals may be present in one or more beds.

The number of theoretical plates is generally in the range from 3 to 25, preferably 5 to 15.

The top pressure in the column K1 is preferably adjusted such that the bottom temperature is within the range specified below.

It is preferable that the bottom temperature is 100° C. or less since it has been found in the context of the present invention that EDMN or EDDN is unstable at relatively high temperatures in the presence of water and decomposes to give unwanted by-products. Preference is given to establishing a bottom temperature in the region of less than 100° C., more preferably less than 80° C. and most preferably less than 60° C. The bottom temperature is preferably in the range from 20 to 100° C., more preferably in the range from 30 to 80° C. and most preferably in the range from 40 to 60° C.

The top pressure is preferably 10 mbar to 1 bar, more preferably 30 mbar to 700 mbar and most preferably 50 to 500 mbar.

In a very particular embodiment, the top pressure in column K1 is less than 300 mbar, more preferably 100 to 200 mbar and most preferably 130 to 180 mbar. In the context of this invention, it has been recognized that the formation of deposits in the column internals, especially the column packings, can be reduced significantly at the temperatures which are established at these top pressures in the column.

In a particularly preferred embodiment, the distillation is performed in the presence of an organic solvent which has a boiling point between water and EDDN and/or EDMN at the distillation pressure existing in the column or which forms a low-boiling azeotrope with water.

This preferred embodiment thus relates to the preparation of EDDN and/or EDMN by conversion of FACH and EDA, the conversion being effected in the presence of water, and the conversion being followed by depletion of water from the reaction mixture in a distillation column, wherein the distillation is performed in the presence of an organic solvent which has a boiling point between water and EDDN and/or EDMN at the distillation pressure existing in the column or which forms a low-boiling azeotrope with water.

The organic solvent which has a boiling point between water and EDDN and/or EDMN at the distillation pressure existing in the column, or which forms a low-boiling azeotrope with water, is referred to hereinafter as distilling agent.

Preferred distilling agents are the organic solvents cited at the outset which have a boiling point between water and EDDN and/or EDMN or which form a low-boiling azeotrope with water.

The distilling agent used is most preferably toluene.

It is preferable that the distilling agent is fed in before or during the conversion of FACH, and EDA. As mentioned above, the amount of organic solvent is generally 0.1 to 50 kg per kg, preferably 1 to 30 kg and more preferably 3 to 25 kg per kg of EDA used.

The amount of distilling agent should generally be such that—as described above—preferably a bottom temperature in the region of less than 100° C., more preferably less than 80° C. and even more preferably less than 70° C. and especially preferably less than 60° C. is established in the column bottom of distillation column K1. The bottom temperature is preferably in the range from 20 to 100° C., more preferably in the range from 30 to 80° C. and most preferably in the range from 40 to 60° C.

It is preferable that the bottom temperature is 100° C. or less since it has been found in the context of the present invention that EDMN or EDDN is unstable at higher temperatures in the presence of water and decomposes to give unwanted by-products.

When the distilling agent forms a low-boiling azeotrope with water, it is necessary that the amount of distilling agent is sufficiently great to be on the right "side" of the azeotrope, which means that the amount of distilling agent must be sufficiently great that the low-boiling aqueous azeotrope is obtained at the top of the column, and essentially no further water is obtained in the column bottoms. The amount of solvent required can be determined in a routine manner by the person skilled in the art, as a function of the distilling agent selected, from commonly known tables and reference works for azeotropes.

The top pressure in column K1 is, as described above, preferably 10 mbar to 1 bar, more preferably 30 mbar to 700 mbar and most preferably 50 to 500 mbar. In a very particular embodiment, the top pressure in column K1 is less than 300 mbar, more preferably 100 to 200 mbar and most preferably 130 to 180 mbar. In the context of this invention, it has been recognized that the formation of deposits in the column internals, especially the column packings, can be reduced significantly at the temperatures which are established at these top pressures in the column.

The condenser of distillation column K1 is generally operated at a temperature at which the predominant portion of the water or of the water azeotrope is condensed at the appropriate top pressure. In general, the operating temperature of the condenser is in the range from 20 to 70° C., preferably 25 to 50° C.

In the condenser, a condensate comprising essentially water or a low-boiling water azeotrope is generally obtained.

The condensate of column K1 can either be discharged or recycled into the process. Before the recycling or discharge, the condensate can optionally be separated into water and distilling agent, for example by distillation. For example, the distillation of water can be performed in the column K2 described above.

If the distilling agent has a miscibility gap with water, the separation of water and distilling agent can also be effected by means of phase separation.

In a preferred embodiment, the vapors from the top of column K1 are supplied to the condenser in which the vapors arising in the flash evaporation are condensed, which means that the vapors from column K1 and from the flash evaporation are preferably conducted to a common condenser.

Reaction Output from Column K1

In the bottom of column K1, the bottom product drawn off is preferably a mixture comprising EDDN or EDMN.

The EDDN- or EDMN-containing mixture preferably comprises the distilling agent used in the distillative depletion of water.

If the distilling agent used is toluene, the EDDN- or EDMN-containing mixture from the bottom of column K1 comprises preferably 5 to 30% by weight of toluene and even more preferably 10 to 20% by weight and especially preferably 12 to 18% by weight, based on the bottoms discharged.

The EDDN- or EDMN-containing mixture from the bottom of column K1 comprises, in the preferred embodiment—in contrast to the amounts of more than 10% by weight described in the prior art—preferably less than 3% by weight, more preferably less than 1% by weight of water, even more preferably less than 0.5% by weight and especially preferably less than 0.3% by weight of water.

The EDDN- or EDMN-containing mixture thus obtained can be hydrogenated directly in a subsequent reaction with hydrogen and in the presence of a catalyst to give DETA or TETA.

Treatment with Adsorbent

In a further particularly preferred embodiment, the EDDN- or EDMN-containing mixture after the water depletion is, however, purified before the hydrogenation of the EDDN or EDMN to give TETA or DETA, by treating the EDDN- or EDMN-containing mixture with an adsorbent.

In a very particularly preferred embodiment, the treatment is effected with a solid acidic adsorbent. In the context of the present invention, it has been found that solid acidic adsorbents can prolong the service life of hydrogenation catalysts in the subsequent hydrogenation to give DETA or TETA. It has also been found that the formation of the aminoethylpiperazine (AEPIP) by-product which occurs in the hydrogenation of EDDN or EDMN and is generally associated with a loss of catalyst activity can be reduced.

This further particularly preferred embodiment thus relates to the preparation of EDDN and/or EDMN by
a) conversion of FACH and EDA, the reaction being effected in the presence of water,
b) depletion of water from the reaction mixture obtained in stage a),
c) treatment of the mixture from stage b) with an adsorbent in the presence of an organic solvent,
wherein the adsorbent is a solid acidic adsorbent.

Stage a)
Processes for conversion of FACH and EDN in the presence of water (stage a)) have been described above.

Stage b)
The depletion of water from the reaction output of the EDDN or EDMN preparation has likewise been described above.

Preferably, low boilers such as HCN or methanol are first removed from the reaction output from the EDDN or EDMN preparation, for example by stripping or flash evaporation, and the water-comprising EDDN or EDMN is subsequently supplied to a distillation in which water is depleted. Most preferably, the distillation, as described above, is effected in the presence of a distilling agent (for definition see above).

Specification: Stage c) Input
The EDDN or EDMN mixture from stage b) comprises preferably 95% by weight of EDDN and/or EDMN or more, more preferably 97% by weight or more, most preferably 99% by weight or more, based on the EDDN mixture minus the distilling agent and/or organic solvent present in the EDDN mixture (calculated "free of distilling agent and free of solvent").

As described above, the mixture obtained from stage b) preferably comprises the distilling agent used in the depletion of water.

If the distilling agent used was toluene, the EDDN or EDMN mixture from stage b) comprises preferably 5 to 30% by weight of toluene, more preferably 10 to 20% by weight of toluene and most preferably 12 to 18% by weight.

If distilling agents which do not have a miscibility gap with EDDN are used, the EDDN or EDMN mixture from stage b) comprises preferably 5 to 50% by weight of EDDN and/or EDMN, more preferably 8 to 30% by weight of EDDN and/or EDMN and most preferably 10 to 20% by weight of EDDN and/or EDMN.

The EDDN or EDMN mixture obtained from stage b) comprises preferably less than 3% by weight, more preferably less than 1% by weight, even more preferably less than 0.5% by weight of water and especially preferably less than 0.3% by weight of water, based on EDDN and EDMN.

Stage c)
In the particularly preferred embodiment, in stage c), the EDDN or EDMN obtained from stage b) is treated with a solid acidic adsorbent in the presence of an organic solvent.

Suitable solvents are all organic solvents which can be used for conversion of EDDN or EDMN. As mentioned above, it is preferable that the organic solvents used are stable under the conditions of the EDDN or EDMN hydrogenation.

Preferably, the organic solvent is supplied with the adsorbent before the treatment of the EDDN or EDMN mixture from stage b).

Preference is given to supplying sufficient organic solvent that the concentration of EDDN and/or EDMN in the mixture which is treated with the adsorbent is in the range from 5 to 50% by weight, more preferably 8 to 30% by weight and most preferably 10 to 20% by weight.

It is also preferable that the water content of organic solvents which are supplied after the EDDN and/or EDMN preparation and before or during the treatment of the EDDN and/or EDMN with adsorbents have a low water content, since it has been found that small amounts of water in the treatment with adsorbent can reduce the absorption capacity of the adsorbent, and polar impurities which lead to unwanted side reactions can be introduced in the subsequent hydrogenation of EDDN or EDMN.

More preferably, the organic solvent fed in comprises less than 0.5% by weight of water, more preferably less than 0.3% by weight of water, even more preferably less than 0.1% by weight of water and especially preferably less than 0.03% by weight of water.

In a very particularly preferred embodiment, THF is fed in as the organic solvent. In the case of use of THF, particularly good catalyst service lives were able to be achieved in the subsequent hydrogenation. If the subsequent hydrogenation is performed in suspension mode, the use of THF can reduce the agglomeration tendency of suspension catalysts during the hydrogenation.

Solid Acidic Adsorbents
In the context of the present invention, a solid acidic adsorbent is understood to mean a water-insoluble porous material which, due to its large surface area, can bind water or other molecules by physical or chemical forces per se.

An acidic adsorbent generally has functional groups which behave as Brønsted or Lewis acids under the conditions of the adsorption. More particularly, an acidic sorbent is capable of retaining preferably basic substances as compared with less basic substances.

Preferred solid acidic adsorbents are acidic metal oxides such as silicon dioxide, titanium dioxide, aluminum oxide, boron oxide ($B_2O_3$), zirconium dioxide, silicates, aluminosilicates, borosilicates, zeolites (especially in the H form), acidic ion exchangers, and silica gel, e.g. Sorbead WS from BASF SE, or mixtures of these substances.

Very particularly preferred solid acidic adsorbents are silicon dioxide and silica gel.

Very particular preference is given to silica gels, which can be produced, for example, by acidifying aqueous sodium waterglass solutions and drying the silica sols obtained at first, as described, for example, in Hollemann-Wiberg (Lehrbuch der Anorganischen Chemie [Inorganic Chemistry], 102nd edition, Walter de Gruyter publishers, 2007, page 962). Examples of particularly preferred silica gels are Sorbead WA from BASF SE and KG 60 silica gel from Merck KGaA.

In a preferred embodiment, the solid acidic adsorbent is a substance selected from the group consisting of silicon dioxide, titanium dioxide, aluminum oxide, boron oxide ($B_2O_3$), zirconium dioxide, silicates, aluminosilicates, borosilicates, zeolites (especially in the H form), acidic ion exchangers and silica gel.

In the context of the present invention, the term "solid acid adsorbent" comprises neither activated carbon nor nonacidic (basic) ion exchangers.

The EDDN or EDMN mixture obtained in stage b) can be treated with organic solvent continuously, semicontinuously or batchwise.

The treatment can be effected batchwise, for example by contacting the adsorbent with the EDDN or EDMN in the presence of an organic solvent. The treatment can be effected by suspending the adsorbent in the mixture to be purified, for example by stirring in a suitable vessel.

The treatment time in the batchwise treatment is generally in the range from 1 minute up to 48 hours, preferably 5 minutes to 24 hours, more preferably 1 hour to 16 hours and especially preferably 2 to 8 hours.

The amount of adsorbent is preferably in the range from 0.1 to 25% by weight, more preferably in the range from 0.5 to 20% by weight and most preferably in the range from 1 to 10% by weight, based on the sum of EDDN, EDMN and organic solvent.

The pressure is generally not critical. However, it is preferable to establish a pressure at which the mixture to be purified is in liquid form. The pressure is generally 1 to 10 bar.

The treatment is effected generally at temperatures of less than 150° C., preferably less than 100° C., more preferably less than 80° C. and especially preferably less than 60° C.

The batchwise treatment with adsorbent can be effected under an inert gas atmosphere, for example under nitrogen or argon.

After the treatment, the adsorbent can be removed from EDDN or EDMN by suitable processes, for example by filtration, centrifugation or sedimentation.

The mixture to be purified is preferably treated continuously.

More preferably, the mixture to be purified is passed through one or more fixed beds or random beds of the adsorbent. The adsorbent may also be arranged in the form of a fluidized bed.

The fixed bed or the random bed is preferably arranged in a tube or a heat exchanger.

The mixture to be purified generally flows through the fixed bed or random bed.

The space velocity is preferably 0.01 to 20, more preferably 0.05 to 15 and most preferably 0.1 to 10 kg of mixture to be purified per kg of adsorbent per hour. The fixed bed volume and the size of the adsorbent particles can be varied within wide ranges and thus adjusted to the selected reaction conditions and the process parameters.

The particle size of the solid acidic adsorbents used is, however, preferably 0.1 to 10, more preferably 0.5 to 6 and most preferably 1 to 4 mm, since it has been found that excessively large particles have adverse diffusion effects, and excessively small particles can lead to blockages in the adsorber. The particles are preferably spherical.

In a preferred variant, the adsorbent is in a fixed bed in carousel arrangement, especially with regeneration, which means that the flow is through two or more alternative fixed beds, and so the unused fixed beds can be regenerated.

The pressure is generally uncritical. However, it is preferable to establish a pressure at which the mixture to be purified is in liquid form. The pressure is generally 1 to 10 bar.

As already described above, the treatment is effected generally at temperatures of less than 150° C., preferably less than 100° C., more preferably less than 80° C. and especially preferably less than 60° C.

The continuous treatment with adsorbent can be effected under an inert gas atmosphere, for example under nitrogen or argon.

If required, after the continuous treatment, the adsorbent or portions of the adsorbent, for example attritus, can be removed from EDDN or EDMN by suitable processes, for example by filtration, centrifugation or sedimentation.

It may be necessary to regenerate the adsorbent after a certain operating time if the efficacy of the adsorbent declines with increasing operating time.

The adsorbent can be regenerated by washing with water, preferably by washing with dilute aqueous acids, more preferably first by washing with water and then by washing with dilute aqueous acids. Preference is given to washing using dilute organic acids, more preferably acetic acid.

The concentration of acids in the dilute aqueous acids is preferably 10% by weight or less.

Preferably, the sorbent after the treatment with water and/or aqueous acid is dried by introducing a dry gas such as air or nitrogen. In the course of drying with a dry gas, preference is given to heating the sorbent and/or the gas.

In a particularly preferred process variant, the sorbent is dried by passing over a dry organic solvent. Particular preference is given to using the same organic solvent which is used in the subsequent hydrogenation, or which is already present in the treatment with adsorbent. The dry organic solvent preferably comprises 1% by weight of water or less, more preferably 0.5% by weight or less, even more preferably 0.1% by weight or less and especially preferably 0.05% by weight or less. The dry organic solvent can be passed over the adsorbent either in liquid or vaporous form.

Preferably, the mixture from stage c) comprises EDDN and/or EDMN together with the organic solvent, in the presence of which the treatment with adsorbent has been performed, and any distilling agent, which was preferably present in the water depletion. The mixture from stage c) may comprise further organic solvents.

The water content of the mixture from stage c) is preferably less than the water content of the EDDN or EDMN mixture before the treatment with adsorbent, since the adsorbent also has a drying effect.

The water content of the mixture from stage c) is preferably 0.1% by weight or less, more preferably 0.03% by weight or less.

The EDDN or EDMN mixture obtained from stage c) can be purified; for example, the organic solvent optionally added can be removed from EDDN or EDMN.

Preferably, however, the mixture obtained from c) is supplied directly—without further workup—to the hydrogenation.

The hydrogenation can be carried out as described below.

Hydrogenation of EDDN or EDMN to Give TETA or DETA

The hydrogenation of EDDN or EDMN to give TETA or DETA, respectively, takes place in general by reaction of EDDN or EDMN with hydrogen in the presence of a catalyst and an organic solvent.

The preparation of EDDN or EDMN takes place preferably—as described above—in accordance with one of the above-described options a) to d), more particularly the preferred embodiments described there.

It is further preferred for the reaction mixture from the preparation of EDDN or EDMN to be cooled, preferably by means of flash evaporation.

It is further preferred for the reaction mixture from the preparation of EDDN or EDMN to be purified, preferably, as described, by depletion of low boilers, preferably by means of flash evaporation, and subsequent distillation for the depletion of water, preferably in the presence of a distillation agent.

It is further preferred for the EDDN or EDMN mixture after the depletion of water to be treated with an adsorbent, preferably, as described, with a solid acidic adsorbent.

The mixture which is introduced into the hydrogenation preferably comprises EDDN and/or EDMN. The fraction of EDDN and/or EDMN in the mixture supplied to the hydrogenation is preferably in the range from 5 to 50% by weight, more preferably 8 to 30% by weight and very preferably 10 to 20% by weight.

The mixture which is introduced into the hydrogenation preferably comprises the organic solvent which was present at the treatment with adsorbent.

Furthermore, the mixture which is introduced into the hydrogenation comprises a distillation agent which preferably was used in the distillative depletion of water.

Hydrogen

The preparation of TETA or DETA takes place in the presence of hydrogen.

The hydrogen is generally used in technical grade purity. The hydrogen can also be used in the form of a hydrogen-comprising gas, i.e. with additions of other inert gases, such as nitrogen, helium, neon, argon or carbon dioxide. The hydrogen-comprising gases used may, for example, be reformer offgases, refinery gases, etc., if and provided that these gases do not comprise any catalyst poisons for the hydrogenation catalysts used, for example CO. However, preference is given to using pure hydrogen or essentially pure hydrogen in the process, for example hydrogen with a content of more than 99% by weight of hydrogen, preferably more than 99.9% by weight of hydrogen, more preferably more than 99.99% by weight of hydrogen, especially more than 99.999% by weight of hydrogen.

Organic Solvent

The preparation of TETA or DETA preferably takes place in the presence of an organic solvent. It is preferred for the organic solvent to be the same solvent that was present at the treatment with adsorbent. It is, however, also possible to add a further solvent or to separate off the solvent which was present during the treatment with adsorbent and to add a new solvent. As organic solvent it is possible to use all organic solvents which can be employed in the preparation of EDDN or EDMN, especially the organic solvents stated as being preferred.

The weight ratio of organic solvent to EDDN or EDMN during the hydrogenation is preferably 0.01:1 to 99:1, more preferably 0.05:1 to 19:1 and most preferably 0.5:1 to 9:1.

However, it is very particularly preferred that the hydrogenation is performed in the presence of THF since the agglomeration tendency of catalysts in suspension mode can be reduced in THF. More preferably, the hydrogenation takes place in the presence of a sufficient amount of THF that the content of EDDN and/or EDMN during the hydrogenation is preferably in the range from 5 to 50% by weight, more preferably 8 to 30% by weight and most preferably 10 to 20% by weight.

It is further preferred that the preparation of EDDN and/or EDMN is effected in the presence of toluene, as described above.

Water

The hydrogenation of EDDN or EDMN can also be effected in the presence of water.

However, it is preferable not to supply any further water since both EDDN and EDMN tend to decompose in the presence of water.

Preference is given to using an EDDN or EDMN comprising less than 3% by weight, preferably less than 1% by weight, more preferably less than 0.5% by weight of water and especially preferably less than 0.3% by weight, based on EDDN or EDMN.

Very particular preference is given to using an EDDN or EDMN comprising less than 0.1% by weight and especially preferably less than 0.03% by weight of water, based on EDDN or EDMN. It is especially preferred that EDDN and/or EDMN is obtained with a low water content by treatment of the EDDN and/or EDMN with adsorbent.

Additive: Basic Compounds

In a further preferred process variant, the hydrogenation takes place in the presence of basic compounds, which are preferably added to the reaction mixture in suitable solvents, such as alkanols, such as C1-C4 alkanols, e.g. methanol or ethanol, or ethers, such as cyclic ethers, e.g. THF or dioxane.

Particular preference is given to adding solutions of alkali metal or alkaline earth metal hydroxides or of hydroxides of the rare earth metals in water, more preferably solutions of LiOH, NaOH, KOH and/or CsOH.

Preference is given to supplying a sufficient amount of alkali metal and/or alkaline earth metal hydroxide that the concentration of alkali metal and/or alkaline earth metal hydroxide based on the mixture to be hydrogenated is in the range from 0.005 to 1% by weight, more preferably 0.01 to 0.5% by weight and most preferably 0.03 to 0.1% by weight.

However, the basic compounds used may also preferably be amides and/or amines, such as ammonia and EDA.

Addition of such basic additives allows the amount of by-products formed, for example AEPIP, in the hydrogenation to be reduced.

Preferred examples of such additives are ammonia and ethylenediamine.

The amount of these additives is 0.01 to 10 mol per mole of EDDN+EDMN.

The basic additives can generally be supplied batchwise or continuously, and before and/or during the hydrogenation.

Catalysts

The catalysts used for hydrogenation of the nitrile function to the amine may be catalysts which comprise, as the active species, one or more elements of transition group 8 of the Periodic Table (Fe, Co, Ni, Ru, Rh, Pd, Os, Ir, Pt), preferably Fe, Co, Ni, Ru or Rh, more preferably Co or Ni.

These include what are called oxidic catalysts, which comprise one or more active species in the form of oxygen compounds thereof, and what are called skeletal catalysts (also referred to as Raney® type; hereinafter also Raney catalyst), which are obtained by leaching (activation) of an alloy composed of hydrogenation-active metal and a further component (preferably Al). The catalysts may additionally comprise one or more promoters.

In a particularly preferred embodiment, in the hydrogenation of EDDN and/or EDMN, Raney catalysts are used, preferably Raney cobalt or Raney nickel catalysts and more preferably Raney cobalt catalysts doped with at least one of the elements Cr, Ni or Fe, or Raney nickel catalysts doped with one of the elements Mo, Cr or Fe.

The catalysts can be used in the form of unsupported catalysts or in supported form. The supports employed preferably include metal oxides such as $Al_2O_3$, $SiO_2$, $ZrO_2$, $TiO_2$, mixtures of metal oxides or carbon (activated carbons, carbon blacks, graphite).

Before use, the oxidic catalysts are activated at elevated temperature by reduction of the metal oxides in a hydrogen-comprising gas stream outside the reactor or within the reactor. If the catalysts are reduced outside the reactor, this may be followed by a passivation by an oxygen-comprising gas stream or embedding into an inert material in order to prevent uncontrolled oxidation under air and to enable safe handling. The inert material used may be organic solvents such as alcohols, or else water or an amine, preferably the reaction product. An exception in terms of activation is that of the skeletal catalysts, which can be activated by leaching with aqueous base, as described, for example, in EP-A 1 209 146.

According to the process performed (suspension hydrogenation, fluidized bed process, fixed bed hydrogenation), the catalysts are used in the form of powder, spall or shaped bodies (preferably extrudates or tablets).

Particularly preferred fixed bed catalysts are the unsupported cobalt catalysts disclosed in EP-A1 742 045, doped with Mn, P and alkali metal (Li, Na, K, Rb, Cs). The catalytically active composition of these catalysts before the reduction with hydrogen consists of 55 to 98% by weight, especially 75 to 95% by weight, of cobalt, 0.2 to 15% by weight of phosphorus, 0.2 to 15% by weight of manganese and 0.05 to 5% by weight of alkali metal, especially sodium, calculated in each case as the oxide.

Further suitable catalysts are the catalysts disclosed in EP-A 963 975, the catalytically active composition of which before the treatment with hydrogen comprises 22 to 40% by weight of $ZrO_2$, 1 to 30% by weight of oxygen compounds of copper, calculated as CuO, 15 to 50% by weight of oxygen compounds of nickel, calculated as NiO, where the molar Ni:Cu ratio is greater than 1, 15 to 50% by weight of oxygen compounds of cobalt, calculated as CoO, 0 to 10% by weight of oxygen compounds of aluminum and/or of manganese, calculated as $Al_2O_3$ and $MnO_2$ respectively, and no oxygen compounds of molybdenum, for example the catalyst A disclosed in this document with the composition of 33% by weight of Zr, calculated as $ZrO_2$, 28% by weight of Ni, calculated as NiO, 11% by weight of Cu, calculated as CuO, and 28% by weight of Co, calculated as CoO.

Additionally suitable are the catalysts disclosed in EP-A 696 572, the catalytically active composition of which before the reduction with hydrogen comprises 20 to 85% by weight of $ZrO_2$, 1 to 30% by weight of oxygen compounds of copper, calculated as CuO, 30 to 70% by weight of oxygen compounds of nickel, calculated as NiO, 0.1 to 5% by weight of oxygen compounds of molybdenum, calculated as $MoO_3$, and 0 to 10% by weight of oxygen compounds of aluminum and/or manganese, calculated as $Al_2O_3$ and $MnO_2$ respectively. For example, the catalyst disclosed specifically in this document with the composition of 31.5% by weight of $ZrO_2$, 50% by weight of NiO, 17% by weight of CuO and 1.5% by weight of $MoO_3$. Equally suitable are the catalysts described in WO-A-99/44984 comprising (a) iron or a compound based on iron or mixtures thereof, (b) from 0.001 to 0.3% by weight, based on (a), of a promoter based on 2, 3, 4 or 5 elements selected from the group of Al, Si, Zr, Ti, V, (c) from 0 to 0.3% by weight, based on (a), of a compound based on an alkali metal and/or alkaline earth metal and d) from 0.001 to 1% by weight, based on (a), of manganese.

For suspension processes, preference is given to using Raney catalysts. In the Raney catalysts, the active catalyst is produced as a "metal sponge" from a binary alloy (nickel, iron, cobalt, with aluminum or silicon) by leaching out one partner with acid or alkali. Residues of the original alloy partner often act synergistically.

The Raney catalysts used for hydrogenation of EDDN and/or EDMN are preferably prepared proceeding from an alloy of cobalt or nickel, more preferably cobalt, and a further alloy component which is soluble in alkalis. In this soluble alloy component, preference is given to using aluminum, but it is also possible to use other components such as zinc and silicon or mixtures of such components.

To activate the Raney catalyst, the soluble alloy component is extracted completely or partially with alkali, for which it is possible to use aqueous sodium hydroxide solution, for example. The catalyst can then be washed, for example with water or organic solvents.

Individual or several further elements may be present in the catalyst as promoters. Examples of promoters are metals of transition groups IB, VIB and/or VIII of the Periodic Table, such as chromium, iron, molybdenum, nickel, copper, etc.

The activation of the catalysts by leaching out the soluble component (typically aluminum) can be effected either in the reactor itself or before introduction into the reactor. The preactivated catalysts are air-sensitive and pyrophoric and are therefore generally stored and handled under a medium, for example water, an organic solvent or a substance present in the subsequent hydrogenation (solvent, reactant, product), or embedded into an organic compound solid at room temperature.

In a preferred embodiment, a Raney cobalt skeletal catalyst is used, which has been obtained from a Co/Al alloy by leaching with aqueous alkali metal hydroxide solution, for example sodium hydroxide solution, and subsequent washing with water, and preferably comprises at least one of the elements Fe, Ni or Cr as promoters.

Such preferred Raney Co catalysts typically comprise, as well as cobalt, also 1-30% by weight of Al, particularly 2-12% by weight of Al, very particularly 3-6% by weight of Al, 0-10% by weight of Cr, particularly 0.1-7% by weight of Cr, very particularly 0.5-5% by weight of Cr, especially 1.5-3.5% by weight of Cr, 0-10% by weight of Fe, particularly 0.1-3% by weight of Fe, very particularly 0.2-1% by weight of Fe, and/or 0-10% by weight of Ni, particularly 0.1-7% by weight of Ni, very particularly 0.5-5% by weight of Ni, especially 1-4% by weight of Ni, where the weight figures are each based on the total catalyst weight.

The catalysts used in the hydrogenation may, for example, advantageously be a "Raney 2724" cobalt skeletal catalyst from W. R. Grace & Co. This catalyst has the following composition: Al: 2-6% by weight, Co: ≥86% by weight, Fe: 0-1% by weight, Ni: 1-4% by weight, Cr: 1.5-3.5% by weight.

Regeneration—General

The catalysts which are used in the reaction of EDDN or EDMN with hydrogen can optionally, in the event of declining activity and/or selectivity, be regenerated by the methods known to those skilled in the art, as published, for example, in WO 99/33561 and documents cited therein.

EP 892777 discloses regenerating deactivated Raney catalysts at temperatures of 150 to 400° C. and pressures of 0.1 to 30 MPa with hydrogen for 2 to 48 hours, in the course of which it is advantageous to wash the catalyst before the actual regeneration with the solvent present in the system, especially with ammonia.

WO 2008/104553 discloses that catalysts which are used for the hydrogenation of TETA or DETA can be regenerated. For regeneration, a process according to WO 99/33561 should be employed.

WO 99/33561 discloses a process for regenerating Raney catalysts, wherein the catalysts are first removed from the reaction medium and the catalyst removed is treated with an aqueous basic solution having a concentration of basic ions of more than 0.01 mol/kg, and the mixture is held at temperatures of less than 130° C. for 1 to 10 hours, optionally in the presence of hydrogen. Subsequently, the catalyst is washed with water or a basic solution until the wash water has a pH in the range from 12 to 13.

The regeneration of the catalyst can be performed in the actual reactor (in situ) or on the deinstalled catalyst (ex situ). In the case of fixed bed processes, preference is given to in situ regeneration.

In the suspension process, preference is likewise given to in situ regeneration.

In this case, the entire catalyst is generally regenerated.

The regeneration is typically effected during a brief shutdown.

Regeneration with Liquid Ammonia and Hydrogen

In a particularly preferred embodiment, Raney catalysts are regenerated by treating the Raney catalysts with liquid ammonia and hydrogen. In this case, the regeneration should be enabled by simple technical means. In addition, the regeneration should be effected with a minimum time requirement in order to reduce shutdown times as a result of catalyst regeneration. Furthermore, the regeneration should enable very substantially complete restoration of the activity of the catalysts used.

This particularly preferred embodiment, accordingly, relates to a process for regenerating Raney catalysts used in the reaction of EDDN or EDMN with hydrogen, and comprises treating the catalyst with liquid ammonia with a water content of less than 5% by weight and with hydrogen having a partial pressure of 0.1 to 40 MPa in the temperature range from 50 to 200° C. for at least 0.1 hour.

In this preferred embodiment, the above-described doped and undoped Raney catalysts are regenerated.

Particular preference is given to using those Raney catalysts which are used in the reaction of EDDN or EDMN with hydrogen.

Especially preferably, this preferred embodiment is used to regenerate Raney Co.

For regeneration, the Raney catalyst is treated with ammonia.

In this particularly preferred embodiment, the ammonia used comprises less than 5% by weight, preferably less than 3% by weight and most preferably less than 1% by weight of water. Such "anhydrous" ammonia is a product which is widely available commercially.

The regeneration can be effected in all reactors which can be used for the hydrogenation of EDDN or EDMN to give TETA or DETA, and which are described below and above. For example, the hydrogenation can be performed in a stirred reactor, jet loop reactor, jet nozzle reactor, bubble column reactor, tubular reactor or else shell and tube reactor, or in a cascade of such identical or different reactors. The hydrogenation can be carried out continuously or batchwise.

In batch mode, the reactor is preferably emptied prior to the treatment with ammonia, by means, for example, of removing the reactor contents from the reactor, by pumping or draining, for example. The emptying of the reactor ought to be very largely complete. Preferably more than 80% by weight, more preferably more than 90% by weight and very preferably more than 95% by weight of the reactor contents ought to be drained off or pumped off.

In continuous mode, the supply of reactants is preferably interrupted and liquid ammonia is instead supplied.

In continuous mode, the liquid ammonia may also originate from condensation reactions within the reactor, for example from the condensation of EDA to give AEPIP.

In this particularly preferred embodiment, the catalyst is treated with liquid ammonia at a temperature of 50 to 350° C., preferably 150 to 300° C., more preferably 200 to 250° C.

The duration of the treatment is preferably 0.1 to 100 hours, preferably 0.1 to 10 hours and more preferably 0.5 to 5 hours.

The weight ratio of amount of ammonia supplied to catalyst is preferably in the range from 1:1 to 1000:1, more preferably in the range from 50:1 to 200:1.

It is additionally preferred that the ammonia is circulated during the treatment with ammonia, for example by pumped circulation or preferably by stirring.

In the particularly preferred embodiment, the treatment of the catalyst with ammonia takes place in the presence of hydrogen. The partial hydrogen pressure in the treatment with ammonia is preferably in the range from 1 to 400 bar, more preferably 5 to 300 bar.

In a particularly preferred embodiment, the concentration of anions in the liquid ammonia is less than 0.01 mol/kg, even more preferably less than 0.0099 mol/kg and especially preferably less than 0.005 mol/kg.

After the treatment with ammonia, ammonia can be removed from the catalyst. This is accomplished, for example, by emptying the reactor and/or by shutting down the ammonia supply.

Before and after the treatment of the Raney catalyst with liquid ammonia, the Raney catalyst can be rinsed once or more than once with organic solvents and/or water.

However, the treatment of the catalyst with organic solvent and/or water after the removal of ammonia or after shutdown of the ammonia supply is not absolutely necessary, since the ammonia is not disruptive in the course of the subsequent hydrogenation and can be discharged continuously from the reactor.

Reaction Conditions in the Hydrogenation

TETA or DETA is generally prepared by reacting EDDN or EDMN with hydrogen in the presence of a hydrogenation catalyst and of an organic solvent.

The temperatures are generally within a range from 60 to 150° C., preferably from 80 to 140° C., especially 100 to 130° C.

The pressure existing in the hydrogenation is generally 5 to 400 bar, preferably 60 to 325 bar, more preferably 100 to 280 bar and especially preferably 170 to 240 bar.

In a particularly preferred embodiment, the pressure in the hydrogenation in the case of use of Raney catalysts is in the range from 170 to 240 bar, since the formation of AEPIP can be reduced within this pressure range. The formation of AEPIP can accelerate the deactivation of the catalyst.

Accordingly, the particularly preferred embodiment relates to a process for preparing TETA and/or DETA by reacting EDDN and/or EDMN with hydrogen in the presence of a catalyst, wherein the catalyst used is a Raney-type catalyst and the pressure in hydrogenation is in the range from 170 to 240 bar.

In a preferred embodiment, EDDN or the aminonitrile mixture comprising EDDN is supplied to the hydrogenation at a rate not greater than the rate with which EDDN and optionally the other components of the aminonitrile mixture reacts with hydrogen in the hydrogenation.

In the hydrogenation of EDDN to TETA, at least four moles of hydrogen are generally required per mole of EDDN.

In the hydrogenation of EDMN to DETA, at least two moles of hydrogen are generally required per mole of EDMN.

Reactor

The reaction of EDDN or EDMN with hydrogen in the presence of catalysts can be performed continuously, semi-continuously or batchwise in customary reaction vessels suitable for catalysis, in a fixed bed, fluidized bed or suspension mode. Suitable reaction vessels for performance of the hydrogenation are those in which contacting of the EDDN or EDMN and of the catalyst with the hydrogen is possible under pressure.

The hydrogenation in suspension mode can be performed in a stirred reactor, jet loop reactor, jet nozzle reactor, bubble column reactor, or in a cascade of such identical or different reactors.

The hydrogenation over a fixed bed catalyst preferably takes place in one or more tubular reactors, or else shell and tube reactors.

The hydrogenation of the nitrile groups takes place with release of heat, which generally has to be removed. The heat can be removed by installed heat transfer surfaces, cooling jackets or external heat transferers in a circuit around the reactor. The hydrogenation reactor or a hydrogenation reactor cascade can be run in straight pass. Alternatively, a circulation mode is also possible, in which a portion of the reactor output is recycled to the reactor inlet, preferably without preceding workup of the circulation stream.

More particularly, the circulation stream can be cooled in a simple and inexpensive manner by means of an external heat transferer, and the heat of reaction can thus be removed.

The reactor can also be operated adiabatically. In the case of adiabatic operation of the reactor, the temperature rise in the reaction mixture can be limited by cooling the feeds or by supplying "cold" organic solvent.

Since the reactor itself need not be cooled in that case, a simple and inexpensive design is possible. One alternative is that of a cooled shell and tube reactor (only in the case of a fixed bed). A combination of the two modes is also conceivable. In this case, a fixed bed reactor is preferably connected downstream of a suspension reactor.

Arrangement of the Catalyst

The catalyst may be arranged in a fixed bed (fixed bed mode) or suspended in the reaction mixture (suspension mode).

Suspension Mode

In a particularly preferred embodiment, the catalyst is suspended in the reaction mixture to be hydrogenated.

The settling rate of the hydrogenation catalyst in the solvent selected should be low in order that the catalyst can be kept in suspension efficiently.

The particle size of the catalysts used in suspension mode is therefore preferably between 0.1 and 500 μm, especially 1 and 100 μm.

If the hydrogenation of EDDN or EDMN is performed continuously in suspension mode, EDDN or EDMN is preferably supplied continuously to the reactor and a stream comprising the hydrogenation products TETA and DETA is removed continuously from the reactor.

In the case of the batchwise suspension mode, EDDN or EDMN, optionally together with organic solvent, is introduced as an initial charge.

The amount of catalyst in the case of the batchwise suspension mode is preferably 1 to 60% by weight, more preferably 5 to 40% by weight and very preferably 20 to 30% by weight, based on the overall reaction mixture.

The residence time in the reactor in the case of the batchwise suspension mode is preferably 0.1 to 6 hours, more preferably 0.5 to 2 hours.

The residence time in the reactor in the case of the continuous suspension mode is preferably 0.1 to 6 hours, more preferably 0.5 to 2 hours.

The space velocity on the catalyst in the case of the continuous suspension mode is preferably 0.1 to 10 kg, preferably 0.5 to 5 kg of EDDN+EDMN per kg of catalyst and hour.

In a particularly preferred embodiment, the space velocity on the catalyst, based on catalyst surface area, is preferably $10^{-6}$ to $10^{-4}$ kg of EDDN+EDMN per m$^2$ of catalyst surface area and hour, the catalyst surface area being determined by the BET method (DIN 66131). The space velocity on the catalyst, based on the catalyst surface area, is more preferably $0.25 \cdot 10^{-5}$ to $5 \cdot 10^{-5}$ kg of EDDN+EDMN per m$^2$ of catalyst surface area and hour and most preferably $0.5 \cdot 10^{-5}$ to $2 \cdot 10^{-5}$ kg of EDDN+EDMN per m$^2$ of catalyst surface area and hour.

The particularly preferred embodiment accordingly relates to a process for preparing TETA and/or DETA by reaction of EDDN and/or EDMN with hydrogen in the presence of a catalyst in the suspension, wherein the space velocity on the catalyst, based on the catalyst surface area, is $10^{-6}$ to $10^{-4}$ kg of EDDN+EDMN per m$^2$ of catalyst surface area and hour, the catalyst surface area being determined by the BET method.

If the reaction is performed in suspension mode in a stirred reactor, the power input via the stirrer is preferably 0.1 to 100 KW per m$^3$.

Spent catalyst can be removed by filtration, centrifugation or crossflow filtration. It may be necessary to compensate for losses of original amount of catalyst resulting from attrition and/or deactivation by adding fresh catalyst.

Fixed Bed Mode

In a further, less preferred embodiment, the catalyst is arranged in a fixed catalyst bed.

The space velocity on the catalyst in the continuous hydrogenation in the fixed bed reactor, for example a tubular reactor or shell and tube reactor, is preferably 0.1 to 10 kg, more preferably 0.5 to 5 kg of EDDN+EDMN per kg of catalyst and hour.

In a particularly preferred embodiment, the space velocity on the catalyst, based on catalyst surface area, is preferably $10^{-6}$ to $10^{-4}$ kg of EDDN+EDMN per m$^2$ of catalyst surface area and hour, the catalyst surface area being determined by the BET method (DIN 66131). The space velocity on the catalyst, based on the catalyst surface area, is more preferably $0.25 \cdot 10^{-5}$ to $5 \cdot 10^{-5}$ kg of EDDN+EDMN per m$^2$ of catalyst surface area and hour and most preferably $0.5 \cdot 10^{-5}$ to $2 \cdot 10^{-5}$ kg of EDDN+EDMN per m$^2$ of catalyst surface area and hour.

The particularly preferred embodiment accordingly relates to a process for preparing TETA and/or DETA by reaction of EDDN and/or EDMN with hydrogen in the presence of a catalyst in the fixed bed, wherein the space velocity on the catalyst, based on the catalyst surface area, is $10^{-6}$ to $10^{-4}$ kg of EDDN+EDMN per m$^2$ of catalyst surface area and hour, the catalyst surface area being determined by the BET method.

In the case of a fixed bed catalyst, it is generally contacted with EDDN or EDMN in liquid phase mode or trickle mode.

Reaction Output

The reaction output from the hydrogenation generally also comprises further higher- and lower-boiling organic substances as by-products, such as methylamine, AEPIP, PIP or TEPA, or basic compounds or additives which have been supplied before or during the hydrogenation, for example alkali metal hydroxides, alkoxides, amides, amines and ammonia.

The hydrogenation output preferably further comprises organic solvent which was present during the hydrogenation, preferably the organic solvent which was also present in the course of treatment with adsorbent, especially THF.

The reaction output preferably further comprises distilling agent, especially toluene, which was preferably used in the distillative depletion of water after the EDDN or EDMN preparation.

The reaction output generally also comprises small amounts of water.

In general, the amounts of water present in the output from the hydrogenation correspond to the amounts which originate from the EDDN or EDMN preparation and the preferred workup.

Purification (General)

After the hydrogenation, the output from the hydrogenation can optionally be purified further.

The catalyst can be removed by methods known to those skilled in the art.

In general, after removal of the catalyst, the hydrogen present during the hydrogenation is removed.

Removal of Hydrogen

Hydrogen is preferably removed by lowering the pressure at which the hydrogenation was performed to a value at which hydrogen is gaseous, but the other components in the reaction output are in liquid phase. The reaction output is preferably decompressed from a hydrogenation pressure of preferably 60 to 325 bar, more preferably 100 to 280 bar and most preferably 170 to 240 bar down to a pressure of 5 to 50 bar in a vessel. At the top of the vessel, hydrogen, with or without ammonia, and a small amount of evaporated low boilers such as THF, are obtained. Hydrogen and any ammonia can be recycled into the hydrogenation of EDDN or EDMN. For example THF can be condensed out and recovered. Alternatively, THF can be recovered by offgas scrubbing with a higher-boiling solvent, for example toluene or TETA.

Removal of the Organic Solvents

Organic solvents present in the reaction output are generally likewise removed by distillation. More particularly, the main products (TETA or DETA) can be isolated from the reaction product together or individually by methods known to those skilled in the art. If the two main products are isolated together, for example by a distillation, they can subsequently be separated into the two individual products. Ultimately, pure TETA and pure DETA are thus obtained. Other impurities, by-products or further ethyleneamines such as TEPA or PIP can likewise be removed from the particular product by methods known to those skilled in the art. Optionally, TETA can also be isolated together with diaminoethylpiperazine or piperazinylethylethylenediamine formed in small amounts.

The hydrogenation outputs from the hydrogenation of EDDN are preferably worked up by distillation.

THF Removal

When the hydrogenation output comprises THF, it is preferable to recycle the THF into the process. More particularly, it is preferable to reuse the THF which was present in the hydrogenation for treatment of EDDN and/or EDMN with adsorbent.

However, it is necessary here that the THF is recycled in virtually anhydrous form, since it has been found that small amounts of water in the treatment with adsorbent can reduce the absorption capacity of the adsorbent, and polar impurities can be introduced in the hydrogenation of EDDN or EDMN, which lead to unwanted side reactions. THF and water, however, form a low-boiling azeotrope.

If the hydrogenation output comprises THF, the removal of water and THF can be effected, for example, in the form of a two-pressure distillation.

In a particularly preferred embodiment, THF is removed by a process for separating a reaction output which is obtained in the reaction of EDDN or EDMN with hydrogen in the presence of THF and of a catalyst and which comprises TETA or DETA and water, with or without organic compounds having higher and lower boiling points than TETA or DETA, wherein i) the reaction output after removal of hydrogen is supplied to a distillation column DK1 in which a THF/water azeotrope is removed via the top and which may also comprise further organic compounds having a lower boiling point than TETA or DETA, and in which a bottom product comprising TETA or DETA is removed, and ii) the bottom product from stage i) is passed into a distillation column DK2 and THF is removed via the top, and a stream comprising TETA or DETA is drawn off at the bottom of the column, and iii) the stream from stage i) drawn off at the top of column DK1 is condensed and an organic solvent which is essentially immiscible with water is fed into the condensate or a portion of the condensate in such an amount that phase separation occurs, and the mixture thus obtained is separated in a phase separator, the organic phase which forms, comprising THF and the organic solvent which is essentially immiscible with water, being recycled into column DK1 and the water phase being discharged.

In the particularly preferred embodiment, hydrogen is first removed from the reaction output. The removal of hydrogen is effected, as described above, preferably by lowering the pressure at which the hydrogenation has been performed to a pressure at which hydrogen is gaseous, but the other components in the reaction output are in the liquid phase. The reaction output is preferably decompressed into a vessel from a hydrogenation pressure of preferably 60 to 325 bar, more preferably 100 to 280 bar and most preferably 170 to 240 bar down to a pressure of 5 to 50 bar. At the top of the vessel, hydrogen, with or without ammonia, and a small amount of vaporized low boilers such as THF, are obtained. Hydrogen and any ammonia can be recycled into the hydrogenation of EDDN or EDMN. THF can be condensed out and recovered. Alternatively, THF can be recovered by offgas scrubbing with a relatively high-boiling solvent, for example toluene or TETA.

In the particularly preferred embodiment, after removal of hydrogen, the reaction output is supplied to a column DK1.

For this purpose, the proportion of the reaction output which has remained in liquid form after the decompression is preferably passed into a column DK1.

The exact operating conditions of the distillation column can, in accordance with the separating performance of the column used, be determined in a routine manner by the person skilled in the art with reference to the known vapor pressures and evaporation equilibria of the components introduced into the distillation column by conventional calculation methods.

The column is preferably configured as a tray column.

In a tray column, there are intermediate trays within the column, on which mass transfer takes place. Examples of different tray types are sieve trays, tunnel-cap trays, dual-flow trays, bubble-cap trays or valve trays.

The column preferably has a stripping section and a rectifying section. However, it may also have only a stripping section.

The number of theoretical plates is generally in the range from 5 to 30, preferably 10 to 20.

The pressure of the column is preferably selected so as to establish a bottom temperature in the range from 100 to 250° C.

The top pressure is preferably 1 to 30 bar, more preferably 3 to 25 bar.

In general, the operating temperature of the condenser is in the range from 30 to 70° C., preferably 35 to 50° C.

In general, low boilers such as ammonia or methylamine are not condensed and are discharged as a gaseous stream. This stream can subsequently be sent to incineration.

In the condenser, the condensate obtained is predominantly the azeotrope of water and THF removed.

In the particularly preferred embodiment, an organic solvent which is essentially immiscible with water and which has, under the distillation conditions in the column DK1, a higher boiling point than the THF/water azeotrope which forms and is drawn off at the top of the column is fed into the condensate or a portion of the condensate.

Organic solvents which are essentially immiscible with water are understood in the context of the present invention to mean those organic solvents in which less than 500 ppm by weight of water can be dissolved.

Preferred organic solvents which are essentially immiscible with water are toluene, n-heptane, n-octane, n-nonane and the like.

Particular preference is given to using those organic solvents which are essentially immiscible with water and which are also preferred solvents in the EDDN or EDMN preparation.

Very particular preference is given to using toluene since it is already used with preference in the EDDN or EDMN preparation.

The amount of essentially water-immiscible organic solvent fed in is generally selected such that phase separation occurs and the phases can be separated by means of the customary technical measures, such as separation in a phase separation vessel.

The weight ratio of essentially water-immiscible organic solvent fed in to condensate is preferably 0.1:1 to 10:1, more preferably 0.5:1 to 5:1 and most preferably 0.8:1 to 2:1.

The mixture of condensate and essentially water-immiscible organic solvent thus obtained is preferably passed into a phase separator, where it separates into an aqueous phase and a phase comprising THF and the essentially water-immiscible solvent.

Preferably, the phase comprising THF and the essentially water-immiscible solvent is recycled into the upper region of column DK1, preferably to the top of column DK1.

Preferably, the entire phase comprising THF and the essentially water-immiscible organic solvent is recycled into the upper region of column DK1.

By virtue of the removal of the water at the top of the column by means of addition of an essentially water-immiscible organic solvent and subsequent phase separation, it is possible to obtain a bottoms output which comprises only small amounts of water. The bottoms output preferably comprises less than 1% by weight, more preferably less than 1000 ppm by weight and more preferably less than 200 ppm by weight of water.

The bottoms output from column DK1 also comprises TETA or DETA, THF, the essentially water-immiscible solvent, with or without further organic solvent (which originates from the dewatering and phase separation), and generally organic by-products such as PIP, AEPIP and TEPA.

In the particularly preferred embodiment, the bottom product from column DK1 is passed into a distillation column DK2 in which THF is removed via the top and, at the bottom of the column, a stream comprising TETA or DETA and the essentially water-immiscible solvent, with or without additional toluene, is drawn off.

The exact operating conditions of the distillation column can, in accordance with the separating performance of the column used, be determined in a routine manner by the person skilled in the art with reference to the known vapor pressures and evaporation equilibria of the components introduced into the distillation column by conventional calculation methods.

The column is preferably configured as a tray column.

In a tray column, there are intermediate trays within the column, on which mass transfer takes place. Examples of different tray types are sieve trays, tunnel-cap trays, dual-flow trays, bubble-cap trays or valve trays.

The column preferably has only a stripping section.

The number of theoretical plates is generally in the range from 5 to 30, preferably 10 to 20.

The top pressure is more preferably 200 mbar to 5 bar, more preferably 500 mbar to 2 bar.

In the column bottom, a temperature above the evaporation temperature of THF is preferably established, such that THF is converted essentially completely to the gas phase.

Particular preference is given to establishing a temperature in the range from 100 to 250° C. at the bottom of the column.

The condenser of distillation column DK2 is generally operated at a temperature at which the predominant portion of the THF is condensed at the appropriate top pressure. In general, the operating temperature of the condenser is in the range from 30 to 70° C., preferably 35 to 50° C.

In the condenser, a condensate comprising essentially THF is obtained. This THF preferably comprises less than 200 ppm by weight, more preferably less than 100 ppm by weight, of water, and so it is particularly suitable for recycling into the workup of the reaction output or of the EDDN or EDMN preparation. It is thus possible to create an integrated system between the EDDN or EDMN hydrogenation and the EDDN or EDMN preparation, which reduces the amounts of organic solvents required.

The condensate at the top of column DK2 may, as well as THF, also comprise traces of the essentially water-immiscible organic solvent. The condensate may nevertheless, as described above, be recycled into the EDDN or EDMN workup, since these solvents, as described above, are likewise a preferred organic solvent in this stage. Preferably, however, the amount of essentially water-immiscible organic solvent in the condensate is reduced by connecting an upstream preliminary condenser at the top of the column, which is operated within the temperature range from 80 to 150° C., preferably 100 to 130° C. Alternatively, the number of plates in the rectifying section of column DK2 can be increased and/or a portion of the condensate can be introduced into the column as reflux. However, it is also possible to reduce the proportion of essentially water-immiscible organic solvent in the top distillate by cooling the feed to column DK2 and/or adjusting the bottom temperature in column DK2 such that only a small amount of the water-immiscible organic solvent is converted into the gas phase.

At the bottom of column DK2, a bottom product comprising TETA or DETA, toluene, and generally the by-products AEPIP, PIP and TEPA, is generally obtained.

In a further particularly preferred embodiment, THF, which is obtained by two-pressure distillation or which is obtained at the top of column DK2 according to the particularly preferred embodiment, is dewatered further with a molecular sieve before being recycled into the process, especially before being recycled into the adsorber stage. The molecular sieve preferably has a pore diameter of less than 4 Å, such that only water and ammonia are retained, and other amines such as methylamine and ethylamine are not. The absorption capacity of the molecular sieve as an adsorbent for the removal of water is increased as a result.

Workup of the Bottom Product

This bottom output can be worked up further by conventional methods and separated into the individual constituents.

In a preferred embodiment, the bottom product from column DK2 is passed into a column DK3 in which a stream comprising predominantly toluene and/or the essentially water-immiscible solvent is drawn off at the top, and the bottom product drawn off is a stream comprising predominantly TETA or DETA, AEPIP, and generally the by-products PIP, AEPIP and TEPA. The exact operating conditions of the distillation column can, in accordance with the separating performance of the column used, be determined in a routine manner by the person skilled in the art with reference to the known vapor pressures and evaporation equilibria of the components introduced into the distillation column by conventional calculation methods.

The distillation column preferably has internals to increase the separating performance. The distillative internals may be present, for example, as a structured packing, for example as a sheet metal packing such as Mellapak 250 Y or Montz Pak, B1-250 type. It is also possible for a packing with a relatively low or increased specific surface area to be present, or it is possible to use a fabric packing or a packing with different geometry such as Mellapak 252 Y.

Advantageous in the case of use of these distillative internals are the low pressure drop and the low specific liquid holdup compared to valve trays, for example. The internals may be present in one or more beds.

The column preferably has a stripping section and a rectifying section.

The bottoms output from column DK2 is preferably supplied in a spatial region between 30% and 90% of the theoretical plates of the distillation column (counted from the bottom), more preferably in a spatial region between 50% and 80% of the theoretical plates of the distillation column. For example, the feed may be somewhat above the middle of the theoretical plates. The optimal feed point can be determined by the person skilled in the art with the customary calculation tools.

The number of theoretical plates is generally in the range from 3 to 25, preferably 5 to 15. Particular preference is given to establishing a temperature at the bottom of the column in the range from 100 to 250° C.

The top pressure is preferably 10 mbar to 1 bar, more preferably 30 mbar to 500 mbar.

The condenser of the distillation column is generally operated at a temperature at which the predominant portion of the toluene and/or of the essentially water-immiscible solvent is condensed at the appropriate top pressure. In general, the operating temperature of the condenser is in the range from 30 to 70° C., preferably 35 to 50° C.

In the condenser, a condensate comprising essentially toluene and/or the essentially water-immiscible organic solvent is obtained. The toluene thus obtained and/or the essentially water-immiscible organic solvent can be recycled into the process, for example by feeding it into the condensate from column DK1. Toluene and/or the essentially water-immiscible organic solvent can, however, also be supplied to the EDDN or EDMN workup, for example upstream of the flash evaporation. In this way, it is possible to achieve an economically viable integrated system.

At the bottom of column DK3, a stream comprising TETA or DETA, and generally the by-products AEPIP, PIP and TEPA, is generally obtained.

This bottoms output can be worked up further by conventional methods and separated into the individual constituents.

In a preferred embodiment, the bottoms output from column DK3 is passed into a column DK4 in which a mixture of PIP, AEPIP and DETA is obtained at the top, a mixture of pentamines such as TEPA and other high boilers is obtained at the bottom, and a TETA stream with a purity of more than 99% by weight is drawn off as a side draw.

The exact operating conditions of the distillation column can, in accordance with the separating performance of the column used, be determined in a routine manner by the person skilled in the art with reference to the known vapor pressures and evaporation equilibria of the components introduced into the distillation column by conventional calculation methods.

The distillation column preferably has internals to increase the separating performance. The distillative internals may be present, for example, as a structured packing, for example as a sheet metal packing such as Mellapak 250 Y or Montz Pak, B1-250 type. It is also possible for a packing with a relatively low or increased specific surface area to be present, or it is possible to use a fabric packing or a packing with different geometry such as Mellapak 252 Y.

Advantageous in the case of use of these distillative internals are the low pressure drop and the low specific liquid holdup compared to valve trays, for example. The internals may be present in one or more beds.

The column preferably has a stripping section and a rectifying section.

The bottoms output from column DK3 is preferably supplied in a spatial region between 30% and 90% of the theoretical plates of the distillation column (counted from the bottom), more preferably in a spatial region between 50% and 80% of the theoretical plates of the distillation column. For example, the feed may be somewhat above the middle of the theoretical plates. The optimal feed point can be determined by the person skilled in the art with the customary calculation tools.

The number of theoretical plates is generally in the range from 5 to 30, preferably 10 to 20.

The top pressure is more preferably 1 mbar to 400 mbar, more preferably 5 mbar to 300 mbar. In the column bottom, preference is given to establishing a temperature above the evaporation temperature of toluene, so that toluene essentially completely converts into the gas phase. Particular preference is given to establishing a temperature in the column bottom in the range from 150 to 250° C.

The condenser of the distillation column is generally operated at a temperature of preferably 30 to 70° C., more preferably 35 to 50° C.

In the condenser, a condensate comprising essentially a mixture of DETA, PIP and AEPIP is obtained.

A portion of the condensate can be recycled into column DK4 are reflux. Preferably 5 to 40% by weight, more preferably 10 to 25% by weight, of the condensate is recycled into column DK4 as reflux.

At the bottom of column DK4, a stream comprising essentially a mixture of pentamines such as TEPA and other high boilers is generally obtained.

TETA is drawn off as a side stream. The side stream is preferably drawn off below the feed line of the bottom stream from column DK4, preferably within the range from 10% to 60%, more preferably in the range from 15 to 35%, of the theoretical plates of the distillation column (counted from the bottom). The side draw comprises preferably more than 99% by weight, more preferably more than 99.5% by weight, of TETA.

The TETA or DETA prepared by the process according to the invention, and the preferred embodiments, is generally of high quality and is thus particularly suitable for further reactions, for example for reaction with epoxy compounds to prepare epoxy resins, or for reaction with acids to prepare amides or polyamides.

The present invention therefore further also provides a process for preparing epoxy resins or amides or polyamides, which comprises in a first stage preparing TETA and/or DETA in accordance with the invention, and in a second stage converting the TETA or DETA thus obtained to epoxy resins, amides or polyamides.

Preferred embodiments of the invention are detailed with reference to the appended drawings.

FIG. 1 shows the preparation of EDDN or EDMN from EDA (1) and FACH (5). The preferred process parameters can be inferred from the above description. First, EDA (1) is mixed with water (2) in a mixer (I) to give an aqueous EDA stream (3). The mixing of EDA with water releases heat of hydration, which is led off in a heat exchanger (II). An FACH-containing stream (5) is mixed with toluene (6). The toluene-containing FACH stream is mixed with the aqueous EDA solution (3) at a mixing point and introduced into an adiabatic tubular reactor (III). At the outlet of the tubular reactor (III), the exiting reaction mixture (7) is decompressed in a decompression valve. The gaseous phase (8) comprising water, toluene and low-boiling compounds which forms is condensed in a condenser (V). Uncondensed constituents (9), such as ammonia, HCN, methanol or $CO_2$, are discharged from the process. The condensate (10) condensed in the condenser (V) is introduced into a phase separation vessel (VI) and separated into an aqueous phase (14) and a toluene-containing phase (11).

The aqueous phase (14) from the phase separation vessel (VI) can be recycled into the process, for example to produce an aqueous EDA solution in the mixer (I), or introduced into a biological waste water treatment (not shown). The aqueous phase (14) can also be introduced into a column K2 (VIII) in which water as a bottom product (16) is removed from low boilers (15). The low boilers (15), for example solvents having a lower boiling point than water or low-boiling water azeotropes or HCN, can be conducted directly to the condenser (V), in which the gaseous phase from the flash evaporation is also condensed. Uncondensable constituents are discharged from the process as stream (9).

The toluene-containing phase (11) can be recycled into the process as an organic solvent and mixed with the FACH-containing stream from the FACH preparation. Losses of toluene can optionally be replaced by a toluene addition. However, the toluene-containing phase (11) can preferably be introduced into a column K1 (VII) together with the liquid phase (12) from the flash vessel (IV).

The phase (12) remaining in liquid form in the flash evaporation is conducted out of the flash vessel (IV) and likewise to the top of column K1 (VII), optionally together with the toluene-containing phase (11), in order to deplete water.

In column K1 (VII), a gaseous, essentially aqueous top product is drawn off and is conducted directly to the condenser (V) and passed into the phase separation vessel (VI). In the phase separation vessel, as described above, aqueous phase (15) which forms can be discharged, passed into the mixer (I) or supplied to column K2 (VIII).

At the bottom (17) of column K1, a mixture of EDDN or EDMN and toluene is drawn off.

The mixture (17) of toluene and EDDN or EDMN is diluted with THF (18) and treated in an adsorber (IX) with adsorbent, preferably with a solid acidic adsorbent. A mixture of EDDN and/or EDMN with toluene and THF (20) obtained from the adsorber comprises only small amounts of water. The EDDN or EDMN mixture can be passed into a hydrogenation in which EDDN or EDMN is hydrogenated to TETA or DETA.

Figure 2:
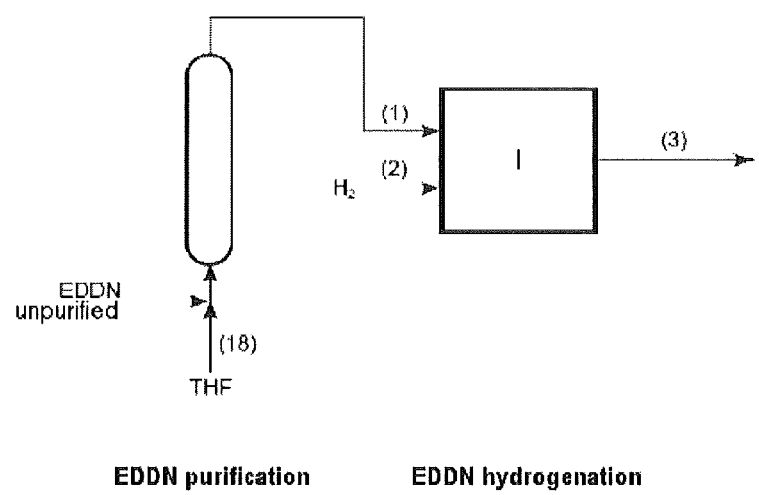
FIG. 2 shows the preparation of TETA or DETA from EDDN or EDMN.

FIG. 2 shows the preparation of TETA or DETA from EDDN or EDMN.

The preferred process parameters can be inferred from the above description.

Figure 3:
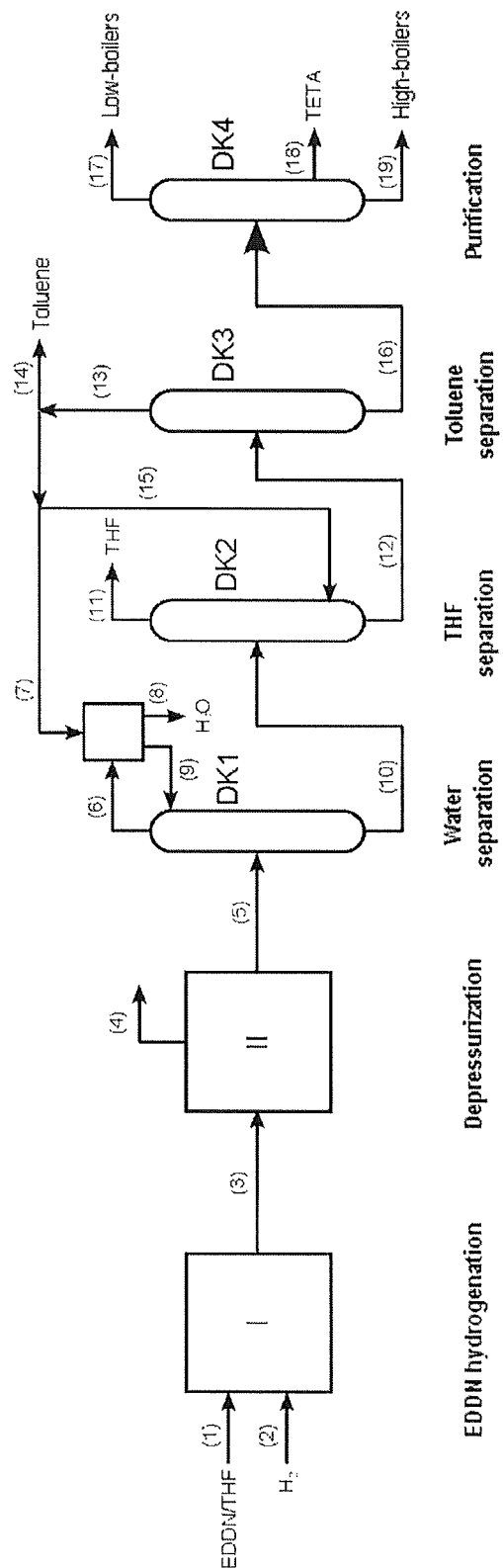
FIG. 3 shows the preparation of TETA or DETA from EDDN or EDMN with subsequent workup.

EDDN or EDMN, which can be prepared by converting FACH and EDA according to one of the options a) to d) cited in the description, and which has been worked up, preferably by i) removal of low boilers, for example by stripping, flash evaporation or distillation, and ii) distillative removal of water, preferably in the presence of an organic solvent which has a boiling point between water and EDDN or EDMN under the conditions of the water removal or which forms a low-boiling azeotrope with water, is referred to in FIG. 3 as "unpurified" EDDN. Such an "unpurified" EDDN or EDMN is mixed with THF (18) and treated in an adsorber with adsorbent, preferably solid acidic adsorbent. The stream (1) which leaves the adsorber is passed into a hydrogenation reactor (1) in which the EDDN or EDMN "purified" by adsorption is hydrogenated in the presence of hydrogen (2) to give TETA or DETA.

FIG. 3 shows the preparation of TETA or DETA from EDDN or EDMN with subsequent workup.

The preferred process parameters can be inferred from the above description.

EDDN or EDMN can be prepared by conversion of FACH and EDA. The workup is effected preferably by i) removal of low boilers, for example by stripping, flash evaporation or distillation, and ii) depletion of water, preferably in the presence of an organic solvent which has a boiling point between water and EDDN or EDMN under the conditions of the water removal, or which forms a low-boiling azeotrope with water.

The dewatered EDDN is preferably mixed with THF and with adsorbent, preferably solid acidic adsorbent. The mixture (1) of EDDN or EDMN and THF is hydrogenated in a hydrogenation reactor (1) in the presence of supplied hydrogen (2) to give TETA or DETA. The reaction output from the hydrogenation (3) is decompressed into a flash vessel (II). The gaseous constituents (4), such as hydrogen, portions of the THF, HCN, methanol or methylamine, can be discharged from the process or recovered partly or fully.

The phase (5) remaining in liquid form after the decompression is passed into a column K1 having a stripping section and a rectifying section. At the top of the column, a low-boiling THF/water azeotrope (6) is drawn off and condensed. The condensed stream is mixed with toluene (7) in a phase separation vessel. In the phase separation vessel, an aqueous phase (8) and a THF/toluene phase (9) form, the latter being recycled into column K1.

From the bottom of column K1, a stream (10) is drawn off which comprises TETA, DETA, THF, toluene and organic compounds such as PIP, AEPIP and TEPA.

This stream (10) is passed into a column K2, in which THF is drawn off as the top product (11). This THF (11) can be recycled directly into the process, preferably into the treatment of EDDN or EDMN with adsorbent. Before being introduced into the adsorber stage, the THF (11) can be contacted with a molecular sieve for further depletion of water.

At the bottom of column K2, a stream (12) is drawn off which comprises TETA, DETA, toluene and organic compounds such as PIP, AEPIP and TEPA.

This stream (12) is introduced into a column K3, in which toluene is drawn off at the top (13). For dewatering of THF, the toluene (13) drawn off can be passed via line (7) into a phase separation vessel in which it is combined with the condensate (6) from column K1. The toluene (13) drawn off can also be discharged from the process via line (14) or preferably used as a solvent in the EDDN and/or EDMN preparation.

The bottom product of column K3 (16) comprises TETA, DETA, toluene and organic compounds such as PIP, AEPIP and TEPA. This mixture can be separated further in column K4. For example, low boilers such as PIP, AEPIP and DETA can be drawn off via the top (17), and TETA can be withdrawn as a side draw (18). High boilers such as TEPA can be drawn off at the bottom (19). The top or bottom stream can be separated into its individual constituents in downstream distillation stages.

ABBREVIATIONS

Ethylenediamine (EDA)
Ethylenediamine-formaldehyde bisadduct (EDFA)
Ethylenediamine-formaldehyde monoadduct (EDMFA)
Ethylenediaminediacetonitrile (EDDN)
Ethylenediaminemonoacetonitrile (EDMN)
Diethylenetriamine (DETA)
Triethylenetetramine (TETA)
Tetraethylenepentamine (TEPA)
Formaldehyde (FA)
Formaldehyde cyanohydrin (FACH)
Piperazine (PIP)
Aminoethylpiperazine (AEPIP)
Mixture of formaldehyde and hydrogen cyanide (GFB)
2- and 3-methyltetrahydrofuran (MeTHF)
Aminoacetonitrile (AAN)

The process of the invention is described in more detail with use of the examples described below.

Analysis

Formaldehyde cyanohydrin (FACH) conversion and hydrogen cyanide conversion were determined by Volhard titration (determination of free cyanide) and Liebig titration (determination of bonded cyanide). Silver nitrate was used for titration in both methods. The yield of useful products was determined by quantitative HPLC analysis (solid phase: 3×Atlantis T3, 5μ, 4.6×250 mm, Waters; mobile phase: 50% by volume of water with 0.5 g/l of ammonium formate, 50% by volume of acetonitrile), using the reaction products and, respectively, comparative substances in each case in the form of pure substance. Useful products stated are the entirety of the α-aminonitriles ethylenediaminediacetonitrile (EDDN), ethylenediaminemonoacetonitrile (EDMN), bicyanomethylimidazoline (BCMI) and ethylenediaminetriacetonitrile (EDTriN). Hazen (APHA) color number and iodine color number (Römpp, Lexikon Chemie [Römpp's chemical encyclopedia], 10th edition, G. Thieme Verlag, 1997, pp. 1285 to 1286) were in each case measured on the aqueous portion of the reaction output optionally after phase separation.

General Preparation Specification for Producing Formaldehyde Cyanohydrin (FACH) in a Stirred Tank Formaldehyde (4880 g, 48.8 mol, 30% by weight in water) was used as initial charge in a 10 l reaction vessel with propeller stirrer, and adjusted to pH 6.5 with sodium hydroxide solution (1 mol/L in water). Within a period of 2 hours, gaseous hydrogen cyanide (1295 g, 47.6 mol, 99% by weight) was metered into the mixture by way of a heated U-tube below the stirrer, while the reaction temperature was kept at 30° C. and pH was kept at 5.5 by adding sodium hydroxide solution. After stirring for a further 45 minutes, pH was adjusted to 2.5 with sulfuric acid (50% by weight in water). Hydrogen cyanide conversion and formaldehyde cyanohydrin content were determined by Volhard and Liebig titrations. Formaldehyde cyanohydrin content was 44% by weight at complete conversion. This solution (density about 950 g/L) was used for the EDDN preparation.

General preparation specification for producing ethylenediaminediacetonitrile (EDDN) from FACH and ethylenediamine (EDA) in an adiabatic tubular reactor:

Examples 1 to 5 described below for producing EDDN from EDA and FACH were carried out in a tubular reactor (length 430 mm, external diameter: 8 mm, internal diameter: 6 mm, upper half of reactor electrically heated, downstream cooling coil), using the bottom process. The reactor comprised a charge of glass beads (diameter 0.4 to 0.6 mm). Volume, taking into account the glass beads, was 5.2 mL.

Example 1

Anhydrous ethylenediamine (233 g/h, 3.88 mol/h, 100% by weight) controlled to room temperature and formaldehyde cyanohydrin (988 g/h, 7.57 mol/h, 44% by weight) cooled to 2° C. were metered by way of two separate pumps into the adiabatic tubular reactor described above. The residence time for said metering rate was 16 s. A temperature of 117° C. was measured at the reactor outlet (ancillary heating, 85° C., pressure 10 bar). The aqueous reaction output was cooled to 0° C. in the downstream cooler and immediately analyzed by Volhard and Liebig titrations, HPLC, and also color number measurement. Volhard and Liebig titrations gave formaldehyde cyanohydrin conversion as 99.3%. Total aminonitrile yield determined by HPLC was 96.1%, based on formaldehyde cyanohydrin used. The Hazen color number of the aqueous solution was 75 (Table 1).

TABLE 1

| RT | Titrations [% by wt.] | | HPLC [% by wt.] | | | | | | | | | CN | |
|---|---|---|---|---|---|---|---|---|---|---|---|---|---|
| [s] | Volhard | Liebig | EDMN | EDDN | BCMI | EDTriN | EDMN | EDDN | BCMI | EDTriN | total | [iodine] | [Hazen] |
| | | | | | | | Yield based on EDA [%] | | | | | | |
| 15 | 0.00 | 0.12 | 3.4 | 36.3 | 2.4 | 0.3 | 10.8 | 82.6 | 5.0 | 0.6 | 98.8 | 0.3 | 75 |
| | | | | | | | Yield based on FACH [%] | | | | | | |
| | | | | | | | 5.5 | 84.7 | 5.1 | 0.8 | 96.1 | | |

Example 2

Anhydrous ethylenediamine (140 g/h, 2.33 mol/h, 100% by weight) controlled to room temperature and formaldehyde cyanohydrin (593 g/h, 4.54 mol/h, 44% by weight) cooled to 2° C. were metered by way of two separate pumps into the adiabatic tubular reactor described above. The residence time for said metering rate was 26 s. A temperature of 117° C. was measured at the reactor outlet (ancillary heating, 85° C., pressure 10 bar). The aqueous reaction output was cooled to 0° C. in the downstream cooler and immediately analyzed by Volhard and Liebig titrations, HPLC, and also color number measurement. Volhard and Liebig titrations gave formaldehyde cyanohydrin conversion as 99.2%. Total aminonitrile yield determined by HPLC was 96.4%, based on formaldehyde cyanohydrin used. The Hazen color number of the aqueous solution was 149 (Table 2).

TABLE 2

| RT [s] | Titrations [% by wt.] | | HPLC [% by wt.] | | | | | | | | | CN | |
|---|---|---|---|---|---|---|---|---|---|---|---|---|---|
| | Volhard | Liebig | EDMN | EDDN | BCMI | EDTriN | EDMN | EDDN | BCMI | EDTriN | total | [iodine] | [Hazen] |
| | | | | | | | Yield based on EDA [%] | | | | | | |
| 25 | 0.00 | 0.13 | 3.2 | 35.7 | 2.6 | 0.8 | 10.2 | 81.3 | 5.4 | 1.4 | 98.4 | 0.7 | 149 |
| | | | | | | | Yield based on FACH [%] | | | | | | |
| | | | | | | | 5.2 | 83.4 | 5.6 | 2.1 | 96.4 | | |

Example 3

Ethylenediamine was diluted with water in a ratio of 3:1 g/g (corresponding to 1:1.1 mol/mol), and the mixture was controlled to room temperature. The aqueous ethylenediamine solution (98 g/h, 1.22 mol/h) and formaldehyde cyanohydrin (310 g/h, 2.37 mol/h, 44% by weight) cooled to 2° C. were metered by way of two separate pumps into the adiabatic tubular reactor described above. The residence time for said metering rate was 47 s. A temperature of 98° C. was measured at the reactor outlet (ancillary heating, 85° C., pressure 10 bar). The aqueous reaction output was cooled to 0° C. in the downstream cooler and immediately analyzed by Volhard and Liebig titrations, HPLC, and also color number measurement. Volhard and Liebig titrations gave formaldehyde cyanohydrin conversion as 98.8%. Total aminonitrile yield determined by HPLC was 93.5%, based on formaldehyde cyanohydrin used. The Hazen color number of the aqueous solution was 72 (Table 3).

amine solution (59 g/h, 0.73 mol/h) and formaldehyde cyanohydrin (186 g/h, 1.43 mol/h, 44% by weight) cooled to 2° C. were metered by way of two separate pumps into the adiabatic tubular reactor described above. The residence time for said metering rate was 78 s. A temperature of 95° C. was measured at the reactor outlet (ancillary heating, 85° C., pressure 10 bar). The aqueous reaction output was cooled to 0° C. in the downstream cooler and immediately analyzed by Volhard and Liebig titrations, HPLC, and also color number measurement. Volhard and Liebig titrations gave formaldehyde cyanohydrin conversion as 98.3%. Total aminonitrile yield determined by HPLC was 93.2%, based on formaldehyde cyanohydrin used. The Hazen color number of the aqueous solution was 247 (Table 4).

TABLE 3

| RT [s] | Titrations [% by wt.] | | HPLC [% by wt.] | | | | | | | | | CN | |
|---|---|---|---|---|---|---|---|---|---|---|---|---|---|
| | Volhard | Liebig | EDMN | EDDN | BCMI | EDTriN | EDMN | EDDN | BCMI | EDTriN | total | [iodine] | [Hazen] |
| | | | | | | | Yield based on EDA [%] | | | | | | |
| 45 | 0.01 | 0.40 | 3.3 | 33.4 | 2.0 | 0.1 | 11.0 | 80.8 | 4.4 | 0.3 | 96.5 | 0.2 | 72 |
| | | | | | | | Yield based on FACH [%] | | | | | | |
| | | | | | | | 5.6 | 82.9 | 4.5 | 0.4 | 93.5 | | |

Example 4

Ethylenediamine was diluted with water in a ratio of 3:1 g/g (corresponding to 1:1.1 mol/mol), and the mixture was controlled to room temperature. The aqueous ethylenedi-

TABLE 4

| RT [s] | Titrations [% by wt.] | | HPLC [% by wt.] | | | | | | | | | CN | |
|---|---|---|---|---|---|---|---|---|---|---|---|---|---|
| | Volhard | Liebig | EDMN | EDDN | BCMI | EDTriN | EDMN | EDDN | BCMI | EDTriN | total | [iodine] | [Hazen] |
| | | | | | | | Yield based on EDA [%] | | | | | | |
| 75 | 0.00 | 0.27 | 2.8 | 33.1 | 2.2 | 0.4 | 9.5 | 80.1 | 4.9 | 0.7 | 95.3 | 1.2 | 247 |
| | | | | | | | Yield based on FACH [%] | | | | | | |
| | | | | | | | 4.9 | 82.1 | 5.1 | 1.1 | 93.2 | | |

Example 5

Ethylenediamine was diluted with toluene in a ratio of 3:1 g/g (corresponding to 4.6:1 mol/mol), and the mixture was controlled to room temperature. The toluene-containing ethylenediamine solution (81 g/h, 1.01 mol/h) and formaldehyde cyanohydrin (257 g/h, 1.97 mol/h, 44% by weight) cooled to 2° C. were metered by way of two separate pumps into the adiabatic tubular reactor described above. The residence time for said metering rate was 63 s. A temperature of 104° C. was measured at the reactor outlet (ancillary heating, 85° C., pressure 10 bar). The aqueous reaction output was cooled to 0° C. in the downstream cooler, and collected in an ice-cooled specimen container. In order to remove the toluene and most of the water, the reaction mixture was then applied continuously by a pump to a Sambay evaporator (jacket temperature: 75° C., pressure: 50-60 mbar, feed rate: 13 mL/min). The bottom product was analyzed by Karl Fischer titration, HPLC, and color number measurement. Karl Fischer titration gave water content as 3.3% by weight. Total aminonitrile yield determined by HPLC was 90.5%, based on formaldehyde cyanohydrin used. The Hazen color number of the water-diluted 30% solution was 396 (Table 5).

TABLE 5

| RT | Titrations [% by wt.] | | HPLC [% by wt.] | | | | | | | | | CN | |
|---|---|---|---|---|---|---|---|---|---|---|---|---|---|
| [s] | Volhard | Liebig | EDMN | EDDN | BCMI | EDTriN | EDMN | EDDN | BCMI | EDTriN | total | [iodine] | [Hazen] |
| | | | | | | | Yield based on EDA [%] | | | | | | |
| 61 | — | — | 8.2 | 80.1 | 4.2 | 1.1 | 11.1 | 77.7 | 3.7 | 0.8 | 93.4 | — | 396 |
| | | | | | | | Yield based on FACH [%] | | | | | | |
| | | | | | | | 5.7 | 79.9 | 3.8 | 1.2 | 90.5 | | |

Example 6

Ethylenediamine (12 g, 0.20 mol) was used as initial charge in a 250 mL reaction vessel, and formaldehyde cyanohydrin (51 g, 0.39 mol) cooled to 0° C. was added dropwise within a period of 60 s. The temperature rose here from 41 to 70° C. Immediately after the addition, the mixture was heated to 80-85° C. by a preheated oil bath. After a total of 120 (Table 6), 180 (Table 7), 300 (Table 8) and 600 s (Table 9)—reaction time including FACH addition time—the solution was analyzed by Volhard and Liebig titrations, HPLC, and color number measurement (Tables 6-9).

TABLE 6

| 120 s | | | | | | | | | | | | | |
|---|---|---|---|---|---|---|---|---|---|---|---|---|---|
| Titrations [% by wt.] | | HPLC [% by wt.] | | | | | | | | | | CN | |
| Volhard | Liebig | EDMN | EDDN | BCMI | EDTriN | EDMN | EDDN | BCMI | EDTriN | total | [iodine] | [Hazen] |
| | | | | | | Yield based on EDA [%] | | | | | | |
| 0.12 | 0.39 | 1.0 | 38.8 | 2.6 | 0.3 | 3.2 | 88.6 | 5.4 | 0.5 | 97.7 | 1.5 | 311 |
| | | | | | | Yield based on FACH [%] | | | | | | |
| | | | | | | 1.6 | 90.8 | 5.6 | 0.8 | 98.8 | | |

TABLE 7

| 180 s | | | | | | | | | | | | | |
|---|---|---|---|---|---|---|---|---|---|---|---|---|---|
| Titrations [% by wt.] | | HPLC [% by wt.] | | | | | | | | | | CN | |
| Volhard | Liebig | EDMN | EDDN | BCMI | EDTriN | EDMN | EDDN | BCMI | EDTriN | total | [iodine] | [Hazen] |
| | | | | | | Yield based on EDA [%] | | | | | | |
| 0.13 | 0.26 | 1.5 | 38.1 | 2.7 | 0.6 | 4.9 | 87.1 | 5.6 | 1.0 | 98.6 | 2.2 | 404 |
| | | | | | | Yield based on FACH [%] | | | | | | |
| | | | | | | 2.5 | 89.3 | 5.8 | 1.6 | 99.2 | | |

TABLE 8

300 s

| Titrations [% by wt.] | | HPLC [% by wt.] | | | | | | | | | CN | |
|---|---|---|---|---|---|---|---|---|---|---|---|---|
| Volhard | Liebig | EDMN | EDDN | BCMI | EDTriN | EDMN | EDDN | BCMI | EDTriN | total | [iodine] | [Hazen] |
| | | | | | | Yield based on EDA [%] | | | | | | |
| 0.11 | 0.17 | 1.7 | 37.7 | 2.7 | 0.8 | 5.3 | 86.1 | 5.7 | 1.4 | 98.5 | 3.4 | 659 |
| | | | | | | Yield based on FACH [%] | | | | | | |
| | | | | | | 2.7 | 88.3 | 5.9 | 2.1 | 99.0 | | |

TABLE 9

600 s

| Titrations [% by wt.] | | HPLC [% by wt.] | | | | | | | | | CN | |
|---|---|---|---|---|---|---|---|---|---|---|---|---|
| Volhard | Liebig | EDMN | EDDN | BCMI | EDTriN | EDMN | EDDN | BCMI | EDTriN | total | [iodine] | [Hazen] |
| | | | | | | Yield based on EDA [%] | | | | | | |
| 0.09 | 0.12 | 2.4 | 36.7 | 2.6 | 1.2 | 7.6 | 83.9 | 5.4 | 2.1 | 99.0 | 8.3 | n.d. |
| | | | | | | Yield based on FACH [%] | | | | | | |
| | | | | | | 3.9 | 86.1 | 5.6 | 3.2 | 98.7 | | |

Example 7

Repeat of Example 2 from WO 2008/104582

Ethylenediamine (132 g, 2.2 mol) was used as initial charge in a 2 L reaction vessel and, with ice cooling, at a temperature of at most 30° C., within a period of 2 h, formaldehyde cyanohydrin (563 g, 4.29 mol) was added dropwise. After continued stirring for 4.5 h, the solution was analyzed by Volhard and Liebig titrations, HPLC, and color number measurement. Volhard and Liebig titrations gave formaldehyde cyanohydrin conversion as 99.8%. Total aminonitrile yield determined by HPLC was 97.6%, based on formaldehyde cyanohydrin used. The iodine color number of the aqueous solution was 10.1. It was no longer possible to determine the Hazen color number (Table 10).

Example 8

700 g/h of formaldehyde (30% by weight in water) and 205 g/h of HCN (90% by weight in water) were passed through an apparatus composed of a circulating reactor of volume 138 mL and of a downstream tubular reactor of volume 19 mL. pH in the circulating reactor was kept constant at 5.5 by adding 28 g/h of NaOH (0.4% by weight in water). The pumped circulation rate in the circulating reactor was 48 kg/h. The temperature in the circulating reactor was adjusted to 30° C. The pressure was 3.2 bar. The temperature measured at the outlet of the tubular reactor was 37° C.

The resultant FACH (stream 5, about 42% by weight in water, density about 950 g/L) was immediately passed with 207 g/h of ethylenediamine (stream 4, pure) and 1.2 kg/h of toluene/organic phase (stream 6) through tubular reactor III of volume 18 mL. Design of apparatus and names of streams and equipment based on FIG. 1). At the outlet of the tubular reactor, the temperature was 93° C. and the pressure was 1.5 bar.

The output from tubular reactor III (stream 7) was immediately passed to the flash vessel IV, with depressurization to 0.2 bar, and cooled to 49° C. during this process. The vapors (stream 8) were passed onward to the condenser V, and the liquid portion (stream 12) was passed to the top of distillation column VII. Column VII comprised 960 mm Montz A3-500 packing with diameter 42 mm. The height of the packing corresponds to about four theoretical plates. The temperature measured at the top of the column was 52° C. The vapors (stream 13) from column VII were likewise condensed at the condenser V. The condensate (stream 10) here broke down into an aqueous (stream 14) and an organic phase (stream 11),

TABLE 10

| Titrations [% by wt.] | | HPLC [% by wt.] | | | | | | | | | CN | |
|---|---|---|---|---|---|---|---|---|---|---|---|---|
| Volhard | Liebig | EDMN | EDDN | BCMI | EDTriN | EDMN | EDDN | BCMI | EDTriN | total | [iodine] | [Hazen] |
| | | | | | | Yield based on EDA [%] | | | | | | |
| 0.01 | 0.05 | 1.8 | 38.6 | 1.9 | 0.0 | 5.9 | 88.2 | 4.1 | 0.0 | 98.2 | 10.1 | n.d. |
| | | | | | | Yield based on FACH [%] | | | | | | |
| | | | | | | 3.0 | 90.4 | 4.2 | 0.0 | 97.6 | | | which were separated in the separator VI. The amount of aqueous phase (stream 14) was 657 g/h. All of this phase was discharged. From the organic phase, a total amount of 4.2 kg/h (stream 11) was returned. 1.2 kg/h thereof (stream 21) were reused for cooling of tubular reactor III, and the remainder was returned to water separation to the top of column VII. Toluene losses were compensated by adding fresh toluene. The temperature at the bottom of column VII was adjusted to 74° C., and the amount drawn off was 558 g/h (stream 17).

The composition of the bottom output (stream 17) was as follows: 15.99% by weight of toluene, 3.17% by weight of EDMN, 69.92% by weight of EDDN, 8.92% by weight of BCMI, 0.31% by weight of EDTriN and 0.15% by weight of water. The iodine color number determined was 10.9.

The yields obtained by way of all of the steps listed above, based on ethylenediamine used, were as follows: 5.2% of EDMN, 82.0% of EDDN, 9.6% of BCMI, 0.3% of EDTriN, giving a total yield of 97.1% of useful products, based on ethylenediamine used.

The examples listed above show that the process of the invention permits conduct of the reaction of FACH with EDA with high conversions and yields. The reaction output obtained has low levels of discoloration and of byproducts. The short residence time in the tubular reactor permits conductivity of the reaction in a relatively small reactor, where temperature can easily be monitored, and in which the rise of reaction temperature can be controlled.

Example 9

Stability of Aqueous EDDN Solutions

Analysis

The useful products were analyzed by quantitative HPLC analysis (solid phase: 3×Atlantis T3, 5µ, 4.6×250 mm, Waters; mobile phase: 50% by volume of water with 0.5 g/L of ammonium formate, 50% by volume of acetonitrile), using the reaction products and, respectively, comparative substances in each case in the form of pure substance.

Stability of 40% by weight of EDDN in water at 40, 60, 80 and 100° C. for up to 600 s:

EDDN (30 g, pure) was dissolved in water (45 g) in a 250 mL round-bottomed flask with thermometer, reflux condenser, and stirrer with precision glass gland. The solution was heated by a preheated oil bath to the temperature stated in Table 11. Specimens were taken at time t=0, 300 and 600 s. EDDN content of each specimen was determined by HPLC, and the color of the mixture was determined by color number measurement.

TABLE 11

| T | EDDN [% by wt.] | | | EDDN [standardized % by wt.] | | |
|---|---|---|---|---|---|---|
| [° C.] | t = 0 s | t = 300 s | t = 600 s | t = 0 s | t = 300 s | t = 600 s |
| 40 | 40.3 | 39.1 | 39.6 | 100.0 | 97.1 | 98.2 |
| 60 | 39.8 | 40.3 | 39.9 | 100.0 | 101.4 | 100.4 |
| 80 | 39.5 | 38.4 | 38.1 | 100.0 | 97.1 | 96.4 |
| 100 | 39.7 | 30.2 | 25.3 | 100.0 | 76.1 | 63.9 |

| T | Color number [iodine] | | | Color number [Gardner] | | |
|---|---|---|---|---|---|---|
| [° C.] | t = 0 s | t = 300 s | t = 600 s | t = 0 s | t = 300 s | t = 600 s |
| 40 | 6.5 | 6.9 | 7.0 | 5.3 | 5.4 | 5.5 |
| 60 | 6.4 | 7.8 | 8.3 | 5.2 | 5.7 | 5.9 |
| 80 | 6.4 | 10.9 | 17.3 | 5.2 | 6.5 | 7.8 |
| 100 | 6.4 | 43.1 | 77.4 | 5.2 | 9.1 | 10.6 |

Stability of 40% by weight of EDDN in water at 40, 60, 80 and 100° C. for up to 120 min:

EDDN (30 g, pure) was dissolved in water (45 g) in a 250 mL round-bottomed flask with thermometer, reflux condenser, and stirrer with precision glass gland. The solution was heated by a preheated oil bath to the temperature stated in Table 12. Specimens were taken at time t=0, 5, 10, 30, 60, 90 and 120 min. EDDN content of each specimen was determined by HPLC, and the color of the mixture was determined by color number measurement (table 12).

TABLE 12

| 40° C. | EDDN | | Color number | |
|---|---|---|---|---|
| t [min] | [% by wt.] | [standardized % by wt.] | [iodine] | [Gardner] |
| 0 | 40.3 | 100.0 | 6.5 | 5.3 |
| 5 | 39.1 | 97.1 | 6.9 | 5.4 |
| 10 | 39.6 | 98.2 | 7.0 | 5.5 |
| 30 | 39.3 | 97.6 | 7.2 | 5.5 |
| 60 | 39.8 | 98.9 | 7.5 | 5.7 |
| 90 | 40.8 | 101.3 | 7.8 | 5.8 |
| 120 | 39.4 | 97.8 | 8.1 | 5.9 |

| 60° C. | EDDN | | Color number | |
|---|---|---|---|---|
| t [min] | [% by wt.] | [standardized % by wt.] | [iodine] | [Gardner] |
| 0 | 39.8 | 100.0 | 6.4 | 5.2 |
| 5 | 40.3 | 101.4 | 7.8 | 5.7 |
| 10 | 39.9 | 100.4 | 8.3 | 5.9 |
| 30 | 37.6 | 94.5 | 12.1 | 6.7 |
| 60 | 37.3 | 93.7 | 79.7 | 10.7 |
| 90 | 36.3 | 91.4 | n.d. | 14.3 |
| 120 | 35.6 | 89.9 | n.d. | 17.0 |

| 80° C. | EDDN | | Color number | |
|---|---|---|---|---|
| t [min] | [% by wt.] | [standardized % by wt.] | [iodine] | [Gardner] |
| 0 | 39.5 | 100.0 | 6.4 | 5.2 |
| 5 | 38.4 | 97.1 | 10.9 | 6.5 |
| 10 | 38.1 | 96.4 | 17.3 | 7.8 |
| 30 | 32.6 | 82.6 | n.d. | 11.7 |
| 60 | 28.5 | 72.2 | n.d. | 16.9 |
| 90 | 22.8 | 57.8 | n.d. | n.d. |
| 120 | 18.7 | 47.3 | n.d. | n.d. |

| 100° C. | EDDN | | Color number | |
|---|---|---|---|---|
| t [min] | [% by wt.] | [standardized % by wt.] | [iodine] | [Gardner] |
| 0 | 39.7 | 100.0 | 6.4 | 5.2 |
| 5 | 30.2 | 76.1 | 43.1 | 9.1 |
| 10 | 25.3 | 63.9 | 77.4 | 10.6 |
| 30 | 18.0 | 45.4 | n.d. | 15.3 |
| 60 | 10.6 | 26.6 | n.d. | 17.5 |
| 90 | 6.1 | 15.3 | n.d. | n.d. |
| 120 | 3.8 | 9.5 | n.d. | n.d. |

Stability of EDDN in 5, 20 and 40% by weight of water at 80° C. for up to 120 min.

The stated amount of water was admixed with EDDN (pure) in a 250 mL round-bottomed flask with thermometer, reflux condenser, and stirrer with precision glass gland. The solution was heated by a preheated oil bath to 80° C. Specimens were taken at time t=0 and 120 min. The color of the mixture of each specimen was determined by color number measurement (Table 13).

TABLE 13

| | Water | | Color number [Gardner] | |
|---|---|---|---|---|
| EDDN [g] | [g] | [% by wt.] | t = 0 min | t = 120 min |
| 80 | — | 0 | 6.0 | 8.6 |
| 76 | 4 | 5 | 5.8 | 14.8 |

TABLE 13-continued

| EDDN [g] | Water [g] | Water [% by wt.] | Color number [Gardner] t = 0 min | Color number [Gardner] t = 120 min |
|---|---|---|---|---|
| 60 | 15 | 20 | 5.2 | n.d. |
| 30 | 45 | 40 | 5.2 | n.d. |

All the references described above are incorporated by reference in its entirety.

The invention claimed is:

1. A process for reacting formaldehyde cyanohydrin (FACH) with ethylenediamine (EDA) in a reactor with limited backmixing at a temperature in the range from 20 to 120° C., wherein the residence time in the reactor is 300 seconds or less.

2. The process according to claim 1, wherein the residence time in the reactor is less than 60 seconds.

3. The process according to claim 1, wherein the reactor is a tubular reactor.

4. The process according to claim 1, wherein the inlet temperature of the reactants into the reactor is in the range from 10 to 50° C.

5. The process according to claim 1, wherein the reaction is effected in the presence of one or more organic solvents.

6. The process according to claim 1, wherein the conversion is performed in the presence of water.

7. The process according to claim 6, wherein at least a portion of the water is mixed with EDA before entry into the reactor and the resulting mixture is then cooled.

8. The process according to claim 1, wherein the reaction mixture is cooled after it leaves the reactor.

9. The process according to claim 1, wherein the reaction mixture is cooled by flash evaporation.

10. The process according to claim 9, wherein the pressure in the flash evaporation step is less than 300 mbar.

11. The process according to claim 5, wherein the organic solvent has a miscibility gap with water.

12. The process according to claim 11, wherein the organic solvent which has a miscibility gap with water is toluene.

13. The process according to claim 1, wherein the tubular reactor is additionally cooled by means of a cooling jacket.

14. The process according to claim 10, wherein the components that are gaseous after the flash evaporation are condensed and separated, in a phase separator, into an aqueous phase and an organic phase, the organic phase being supplied, together with the components that have remained liquid in the flash evaporation, to a distillation means, in which ethylenediaminediacetonitrile (EDDN) or ethylenediaminemonoacetonitrile (EDMN) is taken off as bottom product.

15. A process for preparing diethylenetriamine or triethylenetetramine, which comprises, in a first stage, obtaining ethylenediaminediacetonitrile (EDDN) or ethylenediaminemonoacetonitrile (EDMN) by reacting EDA with FACH according to claim 1, and hydrogenating the EDDN or EDMN obtained in the first stage, using hydrogen in the presence of a catalyst.

16. A process for preparing epoxy resins, amides or polyamides, which comprises in a first stage preparing TETA or DETA by the process according to claim 15, and in a second stage converting the TETA or DETA thus obtained to epoxy resins, amides or polyamides.

17. The process according to claim 1, wherein the residence time in the reactor is less than 180 seconds.

* * * * *